(12) United States Patent
Cummins

(10) Patent No.: US 7,887,563 B2
(45) Date of Patent: *Feb. 15, 2011

(54) SURGICAL STAPLE

(75) Inventor: Christy Cummins, Naas (IE)

(73) Assignee: Abbott Vascular Inc., Santa Clara, CA (US)

( * ) Notice: Subject to any disclaimer, the term of this patent is extended or adjusted under 35 U.S.C. 154(b) by 704 days.

This patent is subject to a terminal disclaimer.

(21) Appl. No.: 11/152,562

(22) Filed: Jun. 14, 2005

(65) Prior Publication Data

US 2005/0267530 A1 Dec. 1, 2005

Related U.S. Application Data

(63) Continuation of application No. 10/240,183, filed on Jan. 22, 2003.

(51) Int. Cl.
A61B 17/08 (2006.01)
(52) U.S. Cl. ...................... 606/219; 606/213
(58) Field of Classification Search ............... 606/219, 606/221, 213, 216, 77; 227/179.1, 181.1, 227/175.1
See application file for complete search history.

(56) References Cited

U.S. PATENT DOCUMENTS

| 287,046 | A | 10/1883 | Norton |
| 438,400 | A | 10/1890 | Brennen |
| 1,088,393 | A | 2/1914 | Backus |
| 1,331,401 | A | 2/1920 | Summers |
| 1,426,111 | A | 8/1922 | Sacker |
| 1,516,990 | A | 11/1924 | Silverman |
| 1,596,004 | A | 8/1926 | De Bengoa |
| 1,647,958 | A | 11/1927 | Ciarlante |
| 1,847,347 | A | 3/1932 | Maisto |
| 1,852,098 | A | 4/1932 | Anderson |
| 1,880,569 | A | 10/1932 | Weis |
| 2,075,508 | A | 3/1937 | Davidson |
| 2,087,074 | A | 7/1937 | Tucker |

(Continued)

FOREIGN PATENT DOCUMENTS

CA 2 339 060 2/2000

(Continued)

OTHER PUBLICATIONS

XP-002199926, Sep. 8, 2000, Anthony et al., Abstract Only.

(Continued)

Primary Examiner—Gary Jackson
Assistant Examiner—Christina Lauer
(74) Attorney, Agent, or Firm—Workman Nydegger

(57) ABSTRACT

In certain exemplary embodiments, a generally U-shaped surgical staple is provided having a base and a pair of legs extending substantially perpendicularly from opposite ends of the base respectively. The legs in use of the staple are bent through approximately 90° relative to the base. To effect a greater compression of the stapled tissue, the legs can include a penetrative portion adjacent the tip and a compressive structure which, due to its increased height relative to that of the penetrative portion, spreads the compressive forces of the staple further along the length of the incision being closed. The compressive portion also provides a depth stop to avoid the tip penetrating too deeply into the tissue in which it is deployed.

23 Claims, 7 Drawing Sheets

U.S. PATENT DOCUMENTS

| | | |
|---|---|---|
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,209,754 A | 10/1965 | Brown |
| 3,142,878 A | 8/1967 | Santora |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A * | 1/1984 | Mericle ............... 606/219 |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,523,695 A | 6/1985 | Braun et al. |
| 4,525,157 A | 6/1985 | Valaincourt |
| 4,526,174 A * | 7/1985 | Froehlich ............... 606/219 |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | Mc Vay |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A * | 10/1989 | Froelich et al. ............... 227/19 |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |

| | | | | | |
|---|---|---|---|---|---|
| 5,131,379 A | 7/1992 | Sewell, Jr. | 5,417,699 A | 5/1995 | Klein et al. |
| 5,147,381 A | 9/1992 | Heimerl | 5,419,777 A | 5/1995 | Hofling |
| 5,156,609 A | 10/1992 | Nakao et al. | 5,423,857 A | 6/1995 | Rosenman et al. |
| 5,158,566 A | 10/1992 | Pianetti | 5,425,489 A | 6/1995 | Shichman et al. |
| 5,160,339 A | 11/1992 | Chen et al. | 5,425,740 A | 6/1995 | Hutchinson, Jr. |
| 5,167,634 A | 12/1992 | Corrigan, Jr. et al. | 5,431,639 A | 7/1995 | Shaw |
| 5,167,643 A | 12/1992 | Lynn | 5,431,667 A | 7/1995 | Thompson et al. |
| 5,171,249 A | 12/1992 | Stefanchik et al. | 5,433,721 A | 7/1995 | Hooven et al. |
| 5,171,250 A | 12/1992 | Yoon | 5,437,631 A | 8/1995 | Janzen |
| 5,171,251 A | 12/1992 | Bregen et al. | 5,439,479 A * | 8/1995 | Shichman et al. ........... 606/220 |
| 5,176,648 A | 1/1993 | Holmes et al. | 5,443,477 A | 8/1995 | Marin et al. |
| 5,176,682 A | 1/1993 | Chow | 5,443,481 A | 8/1995 | Lee |
| 5,192,288 A | 3/1993 | Thompson et al. | 5,449,359 A | 9/1995 | Groiso |
| 5,192,300 A | 3/1993 | Fowler | 5,456,400 A | 10/1995 | Shichman et al. |
| 5,192,301 A | 3/1993 | Kamiya et al. | 5,462,558 A | 10/1995 | Kolesa et al. |
| 5,192,302 A | 3/1993 | Kensey et al. | 5,462,561 A | 10/1995 | Voda |
| 5,192,602 A | 3/1993 | Spencer et al. | 5,466,241 A | 11/1995 | Leroy et al. |
| 5,203,787 A | 4/1993 | Noblitt et al. | 5,470,010 A | 11/1995 | Rothfuss |
| 5,209,756 A | 5/1993 | Seedhorm et al. | 5,474,557 A | 12/1995 | Mai |
| 5,217,024 A | 6/1993 | Dorsey et al. | 5,474,572 A | 12/1995 | Hayhurst |
| 5,219,359 A | 6/1993 | McQuilkin et al. | 5,478,352 A | 12/1995 | Fowler |
| 5,222,974 A | 6/1993 | Kensey et al. | 5,478,353 A | 12/1995 | Yoon |
| 5,226,908 A | 7/1993 | Yoon | 5,478,354 A | 12/1995 | Tovey et al. |
| 5,234,449 A | 8/1993 | Bruker et al. | 5,486,195 A | 1/1996 | Myers et al. |
| 5,236,435 A | 8/1993 | Sewell, Jr. | 5,497,933 A * | 3/1996 | DeFonzo et al. ......... 227/175.1 |
| 5,236,445 A | 8/1993 | Hayhurst et al. | 5,501,698 A | 3/1996 | Roth et al. |
| 5,242,457 A | 9/1993 | Akopov et al. | 5,507,744 A | 4/1996 | Tay et al. |
| 5,242,459 A | 9/1993 | Buelna | 5,507,755 A | 4/1996 | Gresl et al. |
| 5,246,156 A | 9/1993 | Rothfuss et al. | 5,514,159 A | 5/1996 | Matula et al. |
| 5,246,443 A | 9/1993 | Mai | 5,521,184 A | 5/1996 | Zimmermann |
| 5,250,058 A | 10/1993 | Miller et al. | 5,522,840 A | 6/1996 | Krajicek |
| 5,254,105 A | 10/1993 | Haaga | 5,527,322 A | 6/1996 | Klein |
| 5,258,015 A | 11/1993 | Li et al. | 5,536,251 A | 7/1996 | Evard |
| 5,269,792 A | 12/1993 | Kovac et al. | 5,540,712 A | 7/1996 | Kleshinski et al. |
| 5,275,616 A | 1/1994 | Fowler | 5,540,716 A | 7/1996 | Hlavacek |
| 5,282,808 A | 2/1994 | Kovac et al. | 5,543,520 A | 8/1996 | Zimmermann |
| 5,282,827 A | 2/1994 | Kensey et al. | 5,544,802 A | 8/1996 | Crainich |
| 5,282,832 A | 2/1994 | Toso et al. | 5,547,474 A | 8/1996 | Kloeckl et al. |
| 5,289,963 A | 3/1994 | McGarry et al. | 5,560,532 A | 10/1996 | DeFonzo |
| 5,290,243 A | 3/1994 | Chodorow et al. | 5,571,120 A | 11/1996 | Yoon |
| 5,290,310 A | 3/1994 | Makower et al. | 5,575,771 A | 11/1996 | Walinsky |
| 5,292,309 A | 3/1994 | Van Tassel | 5,584,879 A | 12/1996 | Reimold et al. |
| 5,292,332 A | 3/1994 | Lee | 5,591,205 A | 1/1997 | Fowler |
| 5,304,184 A | 4/1994 | Hathaway et al. | 5,593,412 A | 1/1997 | Martinez et al. |
| 5,304,204 A | 4/1994 | Bregen | 5,593,422 A | 1/1997 | Van der Moer et al. |
| 5,306,254 A | 4/1994 | Nash et al. | 5,593,425 A | 1/1997 | Bonutti et al. |
| 5,306,280 A | 4/1994 | Bregen et al. | 5,601,602 A | 2/1997 | Fowler |
| 5,318,542 A | 6/1994 | Hirsch et al. | 5,609,597 A | 3/1997 | Lehrer |
| 5,320,639 A | 6/1994 | Rudnick | 5,611,986 A | 3/1997 | Datta et al. |
| 5,330,442 A | 7/1994 | Green et al. | 5,613,974 A | 3/1997 | Andreas et al. |
| 5,330,445 A | 7/1994 | Haaga | 5,618,291 A | 4/1997 | Thompson et al. |
| 5,334,216 A | 8/1994 | Vidal et al. | 5,618,306 A | 4/1997 | Roth et al. |
| 5,334,217 A | 8/1994 | Das | 5,620,452 A | 4/1997 | Yoon |
| 5,335,680 A | 8/1994 | Moore | 5,620,461 A | 4/1997 | Muijs et al. |
| 5,340,360 A | 8/1994 | Stefanchik | 5,630,824 A | 5/1997 | Hart |
| 5,350,399 A | 9/1994 | Erlebacher et al. | 5,643,318 A | 7/1997 | Tsukernik |
| 5,352,229 A | 10/1994 | Goble et al. | 5,645,553 A | 7/1997 | Kolesa et al. |
| 5,364,406 A | 11/1994 | Sewell, Jr. | 5,645,565 A | 7/1997 | Rudd et al. |
| 5,364,408 A | 11/1994 | Gordon | 5,645,566 A | 7/1997 | Brenneman et al. |
| 5,366,458 A | 11/1994 | Korthoff et al. | 5,645,567 A | 7/1997 | Crainich |
| 5,366,479 A | 11/1994 | McGarry et al. | 5,649,959 A | 7/1997 | Hannam et al. |
| 5,376,101 A | 12/1994 | Green et al. | D383,539 S | 9/1997 | Croley |
| 5,383,896 A | 1/1995 | Gershony et al. | 5,669,917 A | 9/1997 | Sauer et al. |
| 5,383,905 A | 1/1995 | Golds et al. | 5,674,231 A | 10/1997 | Green |
| RE34,866 E | 2/1995 | Kensey et al. | 5,676,689 A | 10/1997 | Kensey et al. |
| 5,391,173 A | 2/1995 | Wilk | 5,676,974 A | 10/1997 | Valdes et al. |
| 5,392,978 A | 2/1995 | Velez | 5,681,334 A | 10/1997 | Evans et al. |
| 5,395,030 A | 3/1995 | Kuramoto | 5,681,351 A | 10/1997 | Jamiolkowski et al. |
| 5,409,499 A | 4/1995 | Yi | 5,683,405 A | 11/1997 | Yacoubian et al. |
| 5,411,520 A | 5/1995 | Nash et al. | 5,690,674 A | 11/1997 | Diaz |
| 5,413,571 A | 5/1995 | Katsaros et al. | 5,695,504 A | 12/1997 | Gifford, III et al. |
| 5,413,584 A | 5/1995 | Schulze | 5,695,505 A | 12/1997 | Yoon |
| 5,416,584 A | 5/1995 | Kay | 5,695,524 A * | 12/1997 | Kelley et al. ................ 606/219 |

| | | | | | |
|---|---|---|---|---|---|
| 5,700,273 A | 12/1997 | Buelna et al. | 5,935,147 A | 8/1999 | Kensey et al. |
| 5,709,708 A | 1/1998 | Thal | 5,938,667 A | 8/1999 | Peyser et al. |
| 5,716,375 A | 2/1998 | Fowler | 5,941,890 A | 8/1999 | Voegele et al. |
| 5,720,755 A | 2/1998 | Dakov | 5,947,999 A | 9/1999 | Groiso |
| 5,720,765 A | 2/1998 | Thal | 5,951,518 A | 9/1999 | Licata et al. |
| 5,725,498 A | 3/1998 | Janzen et al. | 5,951,576 A | 9/1999 | Wakabayashi |
| 5,725,552 A | 3/1998 | Kotula et al. | 5,951,589 A | 9/1999 | Epstein et al. |
| 5,725,554 A | 3/1998 | Simon et al. | 5,957,936 A | 9/1999 | Yoon et al. |
| 5,725,556 A | 3/1998 | Moser et al. | 5,957,938 A | 9/1999 | Zhu et al. |
| 5,728,109 A | 3/1998 | Schulze et al. | 5,964,782 A | 10/1999 | Lafontaine et al. |
| 5,728,110 A | 3/1998 | Vidal et al. | 5,976,159 A | 11/1999 | Bolduc et al. |
| 5,728,114 A | 3/1998 | Evans et al. | 5,976,161 A | 11/1999 | Kirsch et al. |
| 5,728,122 A | 3/1998 | Leschinsky et al. | 5,984,934 A | 11/1999 | Ashby et al. |
| 5,728,132 A | 3/1998 | Van Tassel et al. | 5,984,949 A | 11/1999 | Levin |
| 5,732,872 A | 3/1998 | Bolduc et al. | 5,993,468 A | 11/1999 | Rygaard |
| 5,735,873 A | 4/1998 | MacLean | 5,993,476 A | 11/1999 | Groiso |
| 5,735,875 A | 4/1998 | Bonutti et al. | 6,001,110 A | 12/1999 | Adams |
| 5,735,877 A | 4/1998 | Pagedas | 6,004,341 A | 12/1999 | Zhu et al. |
| 5,749,898 A | 5/1998 | Schulze et al. | 6,007,563 A | 12/1999 | Nash et al. |
| 5,752,966 A | 5/1998 | Chang | 6,013,084 A | 1/2000 | Ken et al. |
| 5,755,726 A | 5/1998 | Pratt et al. | 6,022,372 A | 2/2000 | Kontos |
| 5,755,778 A | 5/1998 | Kleshinski | 6,024,750 A | 2/2000 | Mastri |
| 5,766,217 A | 6/1998 | Christy | 6,024,758 A | 2/2000 | Thal |
| 5,766,246 A | 6/1998 | Mulhauser et al. | 6,030,364 A | 2/2000 | Durgin et al. |
| 5,769,862 A | 6/1998 | Kammerer et al. | 6,030,413 A | 2/2000 | Lazarus |
| 5,769,870 A | 6/1998 | Salahieh et al. | 6,033,427 A | 3/2000 | Lee |
| 5,776,150 A | 7/1998 | Nolan et al. | 6,036,703 A | 3/2000 | Evans et al. |
| 5,779,707 A | 7/1998 | Bertholet et al. | 6,036,720 A | 3/2000 | Abrams et al. |
| 5,782,844 A | 7/1998 | Yoon et al. | 6,045,570 A | 4/2000 | Epstein et al. |
| 5,782,860 A | 7/1998 | Epstein et al. | 6,048,358 A | 4/2000 | Barak |
| 5,782,861 A | 7/1998 | Cragg et al. | 6,056,768 A | 5/2000 | Cates et al. |
| 5,782,864 A | 7/1998 | Lizardi | 6,056,769 A | 5/2000 | Epstein et al. |
| 5,795,958 A | 8/1998 | Rao et al. | 6,056,770 A | 5/2000 | Epstein et al. |
| 5,797,928 A | 8/1998 | Kogasaka | 6,059,800 A | 5/2000 | Hart et al. |
| 5,797,931 A | 8/1998 | Bito et al. | 6,063,085 A | 5/2000 | Tay et al. |
| 5,797,933 A | 8/1998 | Snow et al. | 6,063,114 A | 5/2000 | Nash et al. |
| 5,797,958 A | 8/1998 | Yoon | 6,066,160 A | 5/2000 | Colvin et al. |
| 5,810,776 A | 9/1998 | Bacich et al. | 6,071,300 A | 6/2000 | Brenneman et al. |
| 5,810,846 A | 9/1998 | Virnich | 6,074,409 A | 6/2000 | Goldfarb |
| 5,810,851 A | 9/1998 | Yoon | 6,077,281 A | 6/2000 | Das |
| 5,810,877 A | 9/1998 | Roth et al. | 6,077,291 A | 6/2000 | Das |
| 5,814,069 A | 9/1998 | Schulze et al. | 6,080,182 A | 6/2000 | Shaw et al. |
| 5,817,113 A | 10/1998 | Gifford, III et al. | 6,080,183 A | 6/2000 | Tsugita et al. |
| 5,820,631 A | 10/1998 | Nobles | 6,086,608 A | 7/2000 | Ek et al. |
| 5,827,298 A | 10/1998 | Hart et al. | 6,090,130 A | 7/2000 | Nash et al. |
| 5,830,125 A | 11/1998 | Scribner et al. | 6,092,561 A | 7/2000 | Schmid |
| 5,833,698 A | 11/1998 | Hinchliffe et al. | 6,099,553 A | 8/2000 | Hart et al. |
| 5,843,167 A | 12/1998 | Dwyer et al. | 6,102,271 A | 8/2000 | Longo et al. |
| 5,846,254 A | 12/1998 | Schulze et al. | 6,106,545 A | 8/2000 | Egan |
| 5,853,421 A | 12/1998 | Leschinsky et al. | 6,110,184 A | 8/2000 | Weadock |
| 5,853,422 A | 12/1998 | Huebsch et al. | 6,113,612 A | 9/2000 | Swanson et al. |
| 5,855,312 A | 1/1999 | Toledano | 6,117,125 A | 9/2000 | Rothbarth et al. |
| 5,858,082 A | 1/1999 | Cruz et al. | 6,117,148 A | 9/2000 | Ravo |
| 5,860,991 A | 1/1999 | Klein et al. | 6,120,524 A | 9/2000 | Taheri |
| 5,861,005 A | 1/1999 | Kontos | 6,126,675 A | 10/2000 | Schervinsky et al. |
| 5,868,755 A | 2/1999 | Kanner et al. | 6,126,677 A | 10/2000 | Ganaja et al. |
| 5,868,763 A | 2/1999 | Spence et al. | 6,136,010 A | 10/2000 | Modesitt et al. |
| 5,871,474 A | 2/1999 | Hermann et al. | 6,143,017 A | 11/2000 | Thal |
| 5,871,490 A | 2/1999 | Schulze et al. | 6,149,660 A | 11/2000 | Laufer et al. |
| 5,871,501 A | 2/1999 | Leschinsky et al. | 6,149,667 A | 11/2000 | Hovland et al. |
| 5,871,525 A | 2/1999 | Edwards et al. | 6,152,144 A | 11/2000 | Lesh et al. |
| 5,873,876 A | 2/1999 | Christy | 6,152,934 A | 11/2000 | Harper et al. |
| 5,879,366 A | 3/1999 | Shaw et al. | 6,152,936 A | 11/2000 | Christy et al. |
| 5,893,592 A | 4/1999 | Schulze et al. | 6,152,937 A | 11/2000 | Peterson et al. |
| 5,897,487 A | 4/1999 | Ouchi | 6,159,234 A | 12/2000 | Bonutti et al. |
| 5,902,310 A | 5/1999 | Foerster et al. | 6,165,204 A | 12/2000 | Levinson et al. |
| 5,904,697 A | 5/1999 | Gifford, III et al. | 6,174,324 B1 | 1/2001 | Egan et al. |
| 5,906,631 A | 5/1999 | Imran | 6,193,734 B1 | 2/2001 | Bolduc et al. |
| 5,907,893 A | 6/1999 | Zadno-Azizi et al. | 6,197,042 B1 | 3/2001 | Ginn et al. |
| 5,910,155 A | 6/1999 | Ratcliff et al. | 6,200,329 B1 | 3/2001 | Fung et al. |
| 5,919,207 A | 7/1999 | Taheri | 6,203,565 B1 | 3/2001 | Bonutti et al. |
| 5,919,208 A | 7/1999 | Valenti | 6,206,913 B1 | 3/2001 | Yencho et al. |
| 5,922,009 A | 7/1999 | Epstein et al. | 6,220,248 B1 | 4/2001 | Voegele et al. |

| | | |
|---|---|---|
| 6,221,102 B1 | 4/2001 | Baker et al. |
| 6,231,592 B1 | 5/2001 | Bonutti et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,305,891 B1 | 10/2001 | Burlingame |
| 6,319,258 B1 | 11/2001 | McAllen, III et al. |
| 6,322,580 B1 | 11/2001 | Kanner |
| 6,334,865 B1 | 1/2002 | Redmond et al. |
| 6,348,064 B1 | 2/2002 | Kanner |
| 6,358,258 B1 | 3/2002 | Arcia et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 * | 1/2003 | Kanner ........................ 606/213 |
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 * | 9/2003 | Coleman et al. ............ 606/219 |
| 6,623,509 B2 | 9/2003 | Ginn |
| 6,623,510 B2 | 9/2003 | Carley et al. |
| 6,626,918 B1 | 9/2003 | Ginn et al. |
| 6,632,238 B2 | 10/2003 | Ginn et al. |
| 6,634,537 B2 | 10/2003 | Chen |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 | 8/2005 | Coleman et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,083,635 B2 | 8/2006 | Ginn |
| 7,108,709 B2 * | 9/2006 | Cummins .................... 606/219 |
| 7,108,710 B2 | 9/2006 | Anderson |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,533,790 B1 | 5/2009 | Knodel et al. |
| 7,597,706 B2 * | 10/2009 | Kanner et al. ............... 606/219 |
| D611,144 S | 3/2010 | Reynolds |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026208 A1 | 2/2002 | Belef et al. |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0193808 A1 | 12/2002 | Belef et al. |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0032981 A1 | 2/2003 | Kanner et al. |

| | | | | | | |
|---|---|---|---|---|---|---|
| 2003/0065358 A1 | 4/2003 | Frecker et al. | | 2006/0287674 A1 | 12/2006 | Ginn et al. |
| 2003/0078598 A1 | 4/2003 | Ginn et al. | | 2007/0010853 A1 | 1/2007 | Ginn et al. |
| 2003/0083679 A1 | 5/2003 | Grudem et al. | | 2007/0010854 A1 | 1/2007 | Cummins et al. |
| 2003/0093096 A1 | 5/2003 | McGuckin et al. | | 2007/0021778 A1 | 1/2007 | Carly |
| 2003/0097140 A1 | 5/2003 | Kanner | | 2007/0049967 A1 | 3/2007 | Sibbitt, Jr. et al. |
| 2003/0109890 A1 | 6/2003 | Kanner et al. | | 2007/0049968 A1 | 3/2007 | Sibbitt, Jr. et al. |
| 2003/0125766 A1 | 7/2003 | Ding | | 2007/0060895 A1 | 3/2007 | Sibbitt, Jr. et al. |
| 2003/0158577 A1 | 8/2003 | Pantages et al. | | 2007/0060950 A1 | 3/2007 | Khosravi et al. |
| 2003/0158578 A1 | 8/2003 | Pantages et al. | | 2007/0123817 A1 | 5/2007 | Khosravi et al. |
| 2003/0195504 A1 | 10/2003 | Tallarida et al. | | 2007/0203506 A1 | 8/2007 | Sibbitt, Jr. et al. |
| 2003/0195561 A1 | 10/2003 | Carley et al. | | 2007/0250080 A1 | 10/2007 | Jones et al. |
| 2004/0009205 A1 | 1/2004 | Sawhney | | 2008/0004636 A1 | 1/2008 | Walberg |
| 2004/0009289 A1 | 1/2004 | Carley et al. | | 2008/0009794 A1 | 1/2008 | Bagaoisan et al. |
| 2004/0010285 A1 | 1/2004 | Carley et al. | | 2008/0065151 A1 | 3/2008 | Ginn |
| 2004/0039414 A1 | 2/2004 | Carley et al. | | 2008/0065152 A1 | 3/2008 | Carley |
| 2004/0073236 A1 | 4/2004 | Carley et al. | | 2008/0086075 A1 | 4/2008 | Isik et al. |
| 2004/0073255 A1 | 4/2004 | Ginn et al. | | 2008/0210737 A1 | 9/2008 | Ginn et al. |
| 2004/0082906 A1 | 4/2004 | Tallarida et al. | | 2008/0221616 A1 | 9/2008 | Ginn et al. |
| 2004/0087985 A1 | 5/2004 | Loshakove et al. | | 2008/0269801 A1 | 10/2008 | Coleman et al. |
| 2004/0092964 A1 | 5/2004 | Modesitt et al. | | 2008/0269802 A1 | 10/2008 | Coleman et al. |
| 2004/0092968 A1 | 5/2004 | Caro et al. | | 2008/0272173 A1 | 11/2008 | Coleman et al. |
| 2004/0093027 A1 | 5/2004 | Fabisiak et al. | | 2008/0312686 A1 | 12/2008 | Ellingwood |
| 2004/0097978 A1 | 5/2004 | Modesitt et al. | | 2008/0319475 A1 | 12/2008 | Clark |
| 2004/0127940 A1 | 7/2004 | Ginn et al. | | 2009/0157101 A1 | 6/2009 | Reyes et al. |
| 2004/0143290 A1 | 7/2004 | Brightbill | | 2009/0157102 A1 | 6/2009 | Reynolds et al. |
| 2004/0153122 A1 | 8/2004 | Palermo | | 2009/0157103 A1 | 6/2009 | Walberg et al. |
| 2004/0153123 A1 | 8/2004 | Palermo et al. | | 2009/0254119 A1 | 10/2009 | Sibbitt, Jr. et al. |
| 2004/0158127 A1 | 8/2004 | Okada | | 2010/0130965 A1 | 5/2010 | Sibbitt, Jr. |
| 2004/0158287 A1 | 8/2004 | Cragg et al. | | FOREIGN PATENT DOCUMENTS | | |
| 2004/0167511 A1 | 8/2004 | Buehlmann et al. | | DE | 197 11 288 | 1/1998 |
| 2004/0167570 A1 | 8/2004 | Pantages | | DE | 297 23 736 U 1 | 4/1999 |
| 2004/0191277 A1 | 9/2004 | Sawhney et al. | | DE | 19859952 | 2/2000 |
| 2004/0215232 A1 | 10/2004 | Belhe et al. | | EP | 0 386 361 | 9/1990 |
| 2004/0254591 A1 | 12/2004 | Kanner et al. | | EP | 0 534 696 | 3/1993 |
| 2004/0267193 A1 | 12/2004 | Bagaoisan et al. | | EP | 0 756 851 | 2/1997 |
| 2004/0267308 A1 | 12/2004 | Bagaoisan et al. | | EP | 0 774 237 | 5/1997 |
| 2004/0267312 A1 | 12/2004 | Kanner et al. | | EP | 0 858 776 | 8/1998 |
| 2005/0059982 A1 | 3/2005 | Zung et al. | | EP | 0 941 697 | 9/1999 |
| 2005/0075665 A1 | 4/2005 | Brenzel et al. | | FR | 2 443 238 | 7/1980 |
| 2005/0085851 A1 | 4/2005 | Fiehler et al. | | FR | 2 715 290 | 7/1995 |
| 2005/0085854 A1 | 4/2005 | Ginn | | FR | 2 722 975 | 2/1996 |
| 2005/0085855 A1 | 4/2005 | Forsberg | | FR | 2 768 324 | 3/1999 |
| 2005/0090859 A1 | 4/2005 | Ravlkumar | | GB | 1 358 466 | 7/1974 |
| 2005/0119695 A1 | 6/2005 | Carley et al. | | GB | 2 075 144 | 11/1981 |
| 2005/0121042 A1 | 6/2005 | Belhe et al. | | IE | S 2000/0722 | 10/2001 |
| 2005/0149117 A1 | 7/2005 | Khosravi et al. | | IE | S 2000/0724 | 10/2001 |
| 2005/0165357 A1 | 7/2005 | McGuckin et al. | | IE | S 2001/0547 | 7/2002 |
| 2005/0177189 A1 | 8/2005 | Ginn et al. | | IE | S 2001/0815 | 7/2002 |
| 2005/0216057 A1 | 9/2005 | Coleman et al. | | IE | S 2001/0748 | 8/2002 |
| 2005/0222614 A1 | 10/2005 | Ginn et al. | | IE | S 2001/0749 | 8/2002 |
| 2005/0234508 A1 | 10/2005 | Cummins et al. | | IE | S 2002/0664 | 2/2003 |
| 2005/0245876 A1 | 11/2005 | Khosravi et al. | | IE | S 2002/0665 | 2/2003 |
| 2005/0267528 A1 | 12/2005 | Ginn et al. | | IE | S 2002/0451 | 7/2003 |
| 2005/0273136 A1 | 12/2005 | Belef et al. | | IE | S 2003/0424 | 12/2003 |
| 2005/0273137 A1 | 12/2005 | Ginn | | IE | S 2003/0490 | 1/2004 |
| 2005/0274768 A1 | 12/2005 | Cummins et al. | | IE | S 2004/0368 | 11/2005 |
| 2005/0283188 A1 | 12/2005 | Loshakove et al. | | IE | S 2005/0342 | 11/2005 |
| 2006/0020270 A1 | 1/2006 | Jabba et al. | | JP | 58-181006 | 12/1983 |
| 2006/0034930 A1 | 2/2006 | Khosravi et al. | | JP | 12 74750 | 11/1989 |
| 2006/0047313 A1 | 3/2006 | Khanna et al. | | JP | 11500642 | 8/1997 |
| 2006/0100664 A1 | 5/2006 | Pai et al. | | JP | 2000102546 | 4/2000 |
| 2006/0135989 A1 | 6/2006 | Carley et al. | | NL | 9302140 | 7/1995 |
| 2006/0144479 A1 | 7/2006 | Carley et al. | | PL | 171425 | 4/1997 |
| 2006/0167484 A1 | 7/2006 | Carley et al. | | RU | 2086192 | 8/1997 |
| 2006/0190014 A1 | 8/2006 | Ginn et al. | | SU | 197801 | 6/1967 |
| 2006/0190037 A1 | 8/2006 | Ginn et al. | | SU | 495067 | 12/1975 |
| 2006/0190038 A1 | 8/2006 | Carley et al. | | SU | 912155 | 3/1982 |
| 2006/0195123 A1 | 8/2006 | Ginn et al. | | SU | 1243708 | 7/1986 |
| 2006/0195124 A1 | 8/2006 | Ginn et al. | | SU | 1324650 | 7/1987 |
| 2006/0253037 A1 | 11/2006 | Ginn et al. | | SU | 1405828 | 6/1988 |
| 2006/0253072 A1 | 11/2006 | Pai et al. | | SU | 1456109 | 2/1989 |
| 2006/0265012 A1 | 11/2006 | Anderson | | SU | 1560133 | 4/1990 |

| | | |
|---|---|---|
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2008/031102 | 9/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

"Hand tool for forming telephone connections—comprises pliers with reciprocably driven ram crimping clip around conductors against anvil", Derwent-ACC-No. 1978-B8090A.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, mailed Aug. 27, 2004.
2002/0072768, Office Action, mailed Feb. 23, 2005.
2002/0072768, Office Action, mailed Apr. 11, 2005.
2002/0072768, Office Action, mailed Jul. 27, 2005.
2002/0072768, Office Action, mailed Mar. 6, 2006.
2002/0072768, Office Action, mailed May 24, 2006.
2002/0072768, Office Action, mailed Oct. 26, 2006.
2002/0072768, Office Action, mailed Apr. 19, 2007.
2002/0133193, Office Action, mailed Nov. 4, 2004.
2002/0133193, Office Action, mailed May 4, 2005.
2002/0133193, Office Action, mailed Oct. 18, 2005.
2002/0133193, Notice of Allowance, mailed Apr. 18, 2007.
2002/0133193, Notice of Allowance, mailed Sep. 27, 2007.
2003/0078598, Office Action, mailed Feb. 9, 2005.
2003/0078598, Office Action, mailed May 26, 2005.
2003/0078598, Office Action, mailed Oct. 4, 2005.
2003/0078598, Notice of Allowance, mailed May 10, 2006.
2003/0078598, Notice of Allowance, mailed Jul. 2, 2007.
2003/0195561, Office Action, mailed Jun. 10, 2004.
2003/0195561, Notice of Allowance, mailed Sep. 21, 2004.
2003/0195561, Office Action, mailed Jan. 3, 2006.
2003/0195561, Issue Notification, mailed Feb. 15, 2006.
2003/0195561, Office Action, mailed May 16, 2006.
2003/0195561, Notice of Allowance, mailed Dec. 28, 2006.
2003/0195561, Notice of Allowance, mailed Jul. 10, 2007.
2003/0195561, Notice of Allowance, mailed Aug. 2, 2007.
2004/0153123, Office Action, mailed Sep. 22, 2006.
2004/0153123, Office Action, mailed Jan. 31, 2007.
2004/0153123, Office Action, mailed Sep. 18, 2007.
2004/0153122, Office Action, mailed Nov. 30, 2005.
2004/0153122, Office Action, mailed Aug. 23, 2006.
2004/0153122, Office Action, mailed Feb. 13, 2007.
2004/0153122, Office Action, mailed Sep. 12, 2007.
2004/0073255, Office Action, mailed Sep. 15, 2006.
2004/0073255, Office Action, mailed Apr. 18, 2007.
2004/0073236, Office Action, mailed Sep. 19, 2006.
2004/0073236, Office Action, mailed May 2, 2007.
2004/0009289, Office Action, mailed Jun. 30, 2006.
2004/0009289, Office Action, mailed Oct. 20, 2006.
2004/0009289, Office Action, mailed May 29, 2007.
2004/0167570, Office Action, mailed Oct. 30, 2006.
2004/0167570, Office Action, mailed Apr. 17, 2007.
2004/0167570, Office Action, mailed Aug. 31, 2007.
2005/0274768, Office Action, mailed Oct. 19, 2006.
2005/0274768, Office Action, mailed Aug. 10, 2007.
2005/0216057, Office Action, mailed Feb. 6, 2007.
2005/0216057, Office Action, mailed May 30, 2007.
2005/0234508, Office Action, mailed Aug. 13, 2007.
2006/0135989, Office Action, mailed Nov. 30, 2006.
2006/0135989, Office Action, mailed Sep. 5, 2007.
2006/0195124, Office Action, mailed Jun. 6, 2007.
2006/0195123, Office Action, mailed May 14, 2007.
6,197,042, Notice of Allowance, mailed Nov. 6, 2000.
6,197,042, Issue Notification, mailed Feb. 15, 2001.
6,277,140, Office Action, mailed Mar. 26, 2001.
6,277,140, Notice of Allowance, mailed Jun. 4, 2001.
6,277,140, Issue Notification, mailed Aug. 6, 2001.
6,391,048, Notice of Allowance, mailed Mar. 26, 2001.
6,391,048, Office Action, mailed Sep. 5, 2001.
6,391,048, Notice of Allowance, mailed Feb. 11, 2002.
6,391,048, Issue Notification, mailed May 3, 2002.

6,461,364, Notice of Allowance, mailed May 6, 2002.
6,461,364, Issue Notification, mailed Sep. 19, 2002.
6,582,452, Notice of Allowance, mailed Jan. 31, 2003.
6,582,452, Issue Notification, mailed Jun. 5, 2003.
6,616,686, Office Action, mailed Dec. 17, 2002.
6,616,686, Notice of Allowance, mailed Apr. 21, 2003.
6,616,686, Issue Notification, mailed Aug. 21, 2003.
6,623,510, Notice of Allowance, mailed Apr. 11, 2003.
6,623,510, Office Action, mailed Jun. 9, 2003.
6,623,510, Issue Notification, mailed Sep. 4, 2003.
6,632,238, Office Action, mailed Feb. 26, 2003.
6,632,238, Notice of Allowance, mailed Jun. 16, 2003.
6,632,238, Issue Notification, mailed Sep. 25, 2003.
6,669,714, Office Action, mailed Mar. 4, 2003.
6,669,714, Notice of Allowance, mailed Jul. 28, 2003.
6,669,714, Issue Notification, mailed Dec. 11, 2003.
6,695,867, Notice of Allowance, mailed Sep. 29, 2003.
6,695,867, Issue Notification, mailed Feb. 5, 2004.
6,719,777, Office Action, mailed Feb. 20, 1987.
6,719,777, Notice of Allowance, mailed Jul. 24, 1987.
6,719,777, Issue Notification, mailed Mar. 25, 2004.
6,749,621, Notice of Allowance, mailed Feb. 9, 2004.
6,749,621, Office Action, mailed Apr. 13, 2004.
6,749,621, Issue Notification, mailed May 27, 2004.
6,780,197, Office Action, mailed Sep. 11, 2003.
6,780,197, Office Action, mailed Feb. 9, 2004.
6,780,197, Notice of Allowance, mailed Mar. 17, 2004.
6,780,197, Issue Notification, mailed Aug. 5, 2004.
6,926,731, Office Action, mailed Nov. 16, 2004.
6,926,731, Notice of Allowance, mailed Apr. 6, 2005.
6,926,731, Issue Notification, mailed Jul. 20, 2005.
6,942,674, Office Action, mailed Sep. 29, 2004.
6,942,674, Notice of Allowance, mailed May 13, 2005.
6,942,674, Issue Notification, mailed Aug. 24, 2005.
7,001,398, Office Action, mailed Mar. 22, 2005.
7,001,398, Notice of Allowance, mailed Jul. 6, 2005.
7,001,398, Notice of Allowance, mailed Oct. 5, 2005.
7,001,398, Issue Notification, mailed Feb. 21, 2006.
7,008,435, Office Action, mailed Apr. 20, 2005.
7,008,435, Office Action, mailed Aug. 10, 2005.
7,008,435, Notice of Allowance, mailed Oct. 18, 2005.
7,008,435, Issue Notification, mailed Feb. 15, 2006.
7,108,709, Office Action, mailed Jul. 27, 2004.
7,108,709, Office Action, mailed Dec. 17, 2004.
7,108,709, Notice of Allowance, mailed Mar. 9, 2005.
7,108,709, Office Action, mailed Aug. 11, 2006.
7,108,709, Issue Notification, mailed Aug. 30, 2006.
7,111,768, Office Action, mailed Feb. 23, 2006.
7,111,768, Notice of Allowance, mailed May 31, 2006.
7,111,768, Issue Notification, mailed Sep. 6, 2006.
7,163,551, Office Action, mailed Jan. 10, 2006.
7,163,551, Notice of Allowance, mailed Sep. 20, 2006.
7,163,551, Issue Notification, mailed Dec. 27, 2006.
7,211,101, Office Action, mailed Aug. 10, 2005.
7,211,101, Office Action, mailed Dec. 19, 2005.
7,211,101, Office Action, mailed Apr. 21, 2006.
7,211,101, Notice of Allowance, mailed Dec. 27, 2006.
7,211,101, Issue Notification, mailed Apr. 11, 2007.
2006/0144479, Office Action, mailed Oct. 16, 2007.
Stretch Comb by Scunci, retrieved via internet at www.scunci.com/productdetail by examiner on Oct. 9, 2007, publication date unavailable.
U.S. Appl. No. 12/113,092, filed Apr. 30 , 2008, Ginn et al.
U.S. Appl. No. 12/143,020, filed Jun. 20, 2008, Ellingwood et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.

DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 10/006,400, mailed Apr. 2, 2008, Office Action.
U.S. Appl. No. 10/147,774, mailed Feb. 4, 2008, Notice Of Allowance.
U.S. Appl. No. 10/147,774, mailed Jun. 30, 2008, Office Action.
U.S. Appl. No. 10/264,306, mailed May 26, 2005, Office Action.
U.S. Appl. No. 10/264,306, mailed Feb. 4, 2008, Notice of Allowance.
U.S. Appl. No. 10/264,306, mailed Jun. 27, 2008, Office Action.
U.S. Appl. No. 10/356,214, mailed Mar. 6, 2008, Office Action.
U.S. Appl. No. 10/435,104, mailed Apr. 4, 2008, Notice of Allowance.
U.S. Appl. No. 10/435,104, mailed Sep. 26, 2008, Notice of Allowance.
U.S. Appl. No. 10/517,004, mailed Jan. 30, 2008, Office Action.
U.S. Appl. No. 10/517,004, mailed Aug. 13, 2008, Notice of Allowance.
U.S. Appl. No. 10/541,083, mailed May 5, 2008, Office Action.
U.S. Appl. No. 10/541,083, mailed Sep. 19, 2008, Notice of Allowance.
U.S. Appl. No. 10/616,832, mailed Sep. 17, 2008, Office Action.
U.S. Appl. No. 10/638,115, mailed Feb. 7, 2008, Office Action.
U.S. Appl. No. 10/638,115, mailed Oct. 29, 2008, Office Action.
U.S. Appl. No. 10/667,144, mailed May 12, 2008, Office Action.
U.S. Appl. No. 10/682,459, mailed Apr. 2, 2008, Office Action.
U.S. Appl. No. 10/786,444, mailed Apr. 24, 2008, Office Action.
U.S. Appl. No. 10/786,444, mailed Oct. 17, 2008, Office Action.
U.S. Appl. No. 10/787,073, mailed Feb. 22, 2008, Office Action.
U.S. Appl. No. 11/113,549, mailed Apr. 16, 2008, Office Action.
U.S. Appl. No. 11/198,811, mailed Aug. 26, 2008, Office Action.
U.S. Appl. No. 11/344,891, mailed Apr. 29, 2008, Office Action.
U.S. Appl. No. 11/406,203, mailed May 23, 2008, Notice of Allowance.
U.S. Appl. No. 11/406,203, mailed Sep. 22, 2008, Notice of Allowance.
U.S. Appl. No. 11/411,925, mailed Feb. 5, 2008, Office Action.

U.S. Appl. No. 60/696,069, filed Jul. 1, 2005, Pantages et al.
U.S. Appl. No. 60/946,026, filed Jun. 25, 2007, Ellingwood.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
McCarthy, et al., "Tension (Stay) Suture Bridge", J. of International College of Surgeons, 34(5), pp. 613-614 (Nov. 1960). cited by other.
U.S. Appl. No. 09/680,837, mailed Jul. 9, 2002, Office Action.
U.S. Appl. No. 09/680,837, mailed Nov. 6, 2002, Office Action.
U.S. Appl. No. 09/680,837, mailed Mar. 25, 2003, Office Action.
U.S. Appl. No. 09/680,837, mailed Jun. 16, 2003, Notice of Allowance.
U.S. Appl. No. 09/680,837, mailed Sep. 11, 2003, Issue Notification.
U.S. Appl. No. 10/006,400, mailed Jan. 2, 2009, Office Action.
U.S. Appl. No. 10/147,774, mailed Mar. 18, 2009, Office Action.
U.S. Appl. No. 10/264,306, mailed Feb. 26, 2009, Office Action.
U.S. Appl. No. 10/305,923, mailed Nov. 1, 2004, Office Action.
U.S. Appl. No. 10/305,923, mailed Mar. 3, 2005, Notice of Allowance.
U.S. Appl. No. 10/356,214, mailed Nov. 4, 2008, Office Action.
U.S. Appl. No. 10/435,104, mailed Nov. 14, 2007, Notice of Allowance.
U.S. Appl. No. 10/435,104, mailed Dec. 22, 2008, Notice of Allowance.
U.S. Appl. No. 10/517,004, mailed Feb. 10, 2009, Notice of Allowance.
U.S. Appl. No. 10/541,083, mailed Oct. 31, 2007, Office Action.
U.S. Appl. No. 10/541,083, mailed Dec. 29, 2008, Notice of Allowance.
U.S. Appl. No. 10/667,144, mailed Mar. 24, 2009, Office Action.
U.S. Appl. No. 10/669,313, mailed Oct. 31, 2005, Office Action.
U.S. Appl. No. 10/669,313, mailed Jan. 11, 2006, Notice of Allowance.
U.S. Appl. No. 10/669,313, mailed Jun. 28, 2006, Notice of Allowance.
U.S. Appl. No. 10/669,313, mailed Nov. 15, 2006, Issue Notification.
U.S. Appl. No. 10/682,459, mailed Dec. 4, 2008, Office Action.
U.S. Appl. No. 10/787,073, mailed Nov. 12, 2008, Office Action.
U.S. Appl. No. 10/908,721, mailed Nov. 25, 2008, Office Action.
U.S. Appl. No. 11/048,503, mailed Mar. 13, 2009, Office Action.
U.S. Appl. No. 11/344,793, mailed Jan. 22, 2009, Office Action.
U.S. Appl. No. 11/344,868, mailed Mar. 25, 2009, Office Action.
U.S. Appl. No. 11/344,891, mailed Dec. 8, 2008, Office Action.
U.S. Appl. No. 11/344,891, mailed Feb. 26, 2009, Office Action.
U.S. Appl. No. 11/396,731, mailed Feb. 13, 2009, Office Action.
U.S. Appl. No. 11/406,203, mailed Mar. 3, 2009, Office Action.
U.S. Appl. No. 11/411,925, mailed Jan. 12, 2009, Office Action.
U.S. Appl. No. 11/427,297, mailed Jan. 30, 2009, Office Action.
U.S. Appl. No. 11/461,323, mailed May 2, 2007, Office Action.
U.S. Appl. No. 11/461,323, mailed Oct. 29, 2007, Office Action.
U.S. Appl. No. 11/461,323, mailed Apr. 25, 2008, Office Action.
U.S. Appl. No. 11/461,323, mailed Nov. 6, 2008, Office Action.
U.S. Appl. No. 11/532,325, mailed Feb. 23, 2009, Office Action.
U.S. Appl. No. 11/744,089, mailed Nov. 26, 2008, Office Action.
U.S. Appl. No. 12/106,928, mailed Jan. 23, 2009, Office Action.
U.S. Appl. No. 12/106,937, mailed Mar. 30, 2009, Office Action.
U.S. Appl. No. 29/296,370, mailed Aug. 18, 2008, Office Action.
U.S. Appl. No. 29/296,370, mailed Dec. 2, 2008, Notice of Allowance.
U.S. Appl. No. 29/296,370, mailed Apr. 1, 2009, Notice of Allowance.
U.S. Appl. No. 10/006,400, mailed Aug. 2, 2010, Notice of Allowance.
U.S. Appl. No. 10/147,774, mailed Jun. 8, 2010, Office Action.
U.S. Appl. No. 10/264,306, mailed Jun. 15, 2010, Office Action.
U.S. Appl. No. 10/435,104, mailed Jul. 23, 2009, Notice of Allowance.
U.S. Appl. No. 10/435,104, mailed Jun. 2, 2010, Office Action.
U.S. Appl. No. 10/517,004, mailed Aug. 3, 2010, Notice of Allowance.
U.S. Appl. No. 10/667,144, mailed Jun. 22, 2010, Office Action.

U.S. Appl. No. 11/048,503, mailed Jul. 30, 2010, Notice of Allowance.
U.S. Appl. No. 11/113,549, mailed Jul. 6, 2010, Office Action.
U.S. Appl. No. 11/198,811, mailed Jun. 29, 2010, Notice of Allowance.
U.S. Appl. No. 11/390,586, mailed Jul. 6, 2010, Office Action.
U.S. Appl. No. 11/396,731, mailed Jun. 29, 2010, Office Action.
U.S. Appl. No. 11/767,818, mailed Dec. 24, 2009, Office Action.
U.S. Appl. No. 11/767,818, mailed Mar. 22, 2010, Office Action.
U.S. Appl. No. 11/852,190, mailed Jun. 24, 2010, Office Action.
U.S. Appl. No. 11/959,334, mailed Jul. 23, 2010, Notice of Allowance.
U.S. Appl. No. 12/113,851, mailed Jun. 24, 2010, Office Action.
U.S. Appl. No. 12/403,277, mailed Jul. 8, 2010, Office Action.
U.S. Appl. No. 10/006,400, mailed Jul. 9, 2009, Notice of Allowance.
U.S. Appl. No. 10/264,306, mailed Aug. 13, 2009, Office Action.
U.S. Appl. No. 10/356,214, mailed Apr. 29, 2009, Office Action.
U.S. Appl. No. 10/517,004, mailed Jun. 26, 2009, Notice of Allowance.
U.S. Appl. No. 10/541,083, mailed Apr. 16, 2009, Notice of Allowance.
U.S. Appl. No. 10/616,832, mailed Jul. 21, 2009, Office Action.
U.S. Appl. No. 10/638,115, mailed May 7, 2009, Notice of Allowance.
U.S. Appl. No. 10/682,459, mailed Jun. 10, 2009, Office Action.
U.S. Appl. No. 10/786,444, mailed Jun. 18, 2009, Office Action.
U.S. Appl. No. 10/787,073, mailed Aug. 13, 2009, Office Action.
U.S. Appl. No. 10/908,721, mailed Jun. 23, 2009, Office Action.
U.S. Appl. No. 11/048,503, mailed Jun. 26, 2009, Office Action.
U.S. Appl. No. 11/113,549, mailed Jul. 21, 2009, Office Action.
U.S. Appl. No. 11/390,586, mailed Jun. 24, 2009, Office Action.
U.S. Appl. No. 11/396,141, mailed May 22, 2009, Restriction Requirement.
U.S. Appl. No. 11/396,141, mailed Aug. 26, 2009, Office Action.
U.S. Appl. No. 11/396,731, mailed May 22, 2009, Office Action.
U.S. Appl. No. 11/406,203, mailed Sep. 16, 2009, Office Action.
U.S. Appl. No. 11/411,925, mailed Sep. 10, 2009, Office Action.
U.S. Appl. No. 11/427,297, mailed Sep. 15, 2009, Office Action.
U.S. Appl. No. 11/461,323, mailed Jul. 27, 2009, Office Action.
U.S. Appl. No. 11/532,325, mailed Jun. 17, 2009, Office Action.
U.S. Appl. No. 11/744,089, mailed Aug. 14, 2009, Office Action.
U.S. Appl. No. 11/958,295, mailed Aug. 27, 2009, Office Action.
U.S. Appl. No. 10/147,774, mailed Oct. 26, 2009, Office Action.
U.S. Appl. No. 10/541,083, mailed Sep. 30, 2009, Notice of Allowance.
U.S. Appl. No. 11/198,811, mailed Sep. 22, 2009, Office Action.
U.S. Appl. No. 11/344,891, mailed Oct. 7, 2009, Office Action.
U.S. Appl. No. 12/106,928, mailed Oct. 5, 2009, Office Action.
U.S. Appl. No. 60/693,531, filed Jun. 24, 2005, Carly.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
Marshall A.C., Lock J.E., Structural and Compliant Anatomy of the Patent Foramen Ovale in Patients Undergoing Transcatheter Closure, Am Heart J Aug. 2000; 140(2); pp. 303-7.
Taber's Cyclopedic Medical Dictionary, 18th Ed. 1997, pp. 747 and 1420.
U.S. Appl. No. 10/006,400, mailed Jan. 13, 2010, Notice of Allowance.
U.S. Appl. No. 10/006,400, mailed Apr. 27, 2010, Notice of Allowance.
U.S. Appl. No. 10/264,306, mailed Jan. 27, 2010, Office Action.
U.S. Appl. No. 10/356,214, mailed Jan. 13, 2010, Notice of Allowance.
U.S. Appl. No. 10/356,214, mailed May 13, 2010, Notice of Allowance.
U.S. Appl. No. 10/435,104, mailed Jan. 20, 2010, Notice of Allowance.
U.S. Appl. No. 10/517,004, mailed Jan. 11, 2010, Notice of Allowance.
U.S. Appl. No. 10/517,004, mailed Apr. 23, 2010, Notice of Allowance.
U.S. Appl. No. 10/541,083, mailed Feb. 5, 2010, Notice of Allowance.
U.S. Appl. No. 10/541,083, mailed May 10, 2010, Notice of Allowance.
U.S. Appl. No. 10/616,832, mailed Jan. 11, 2010, Notice of Allowance.
U.S. Appl. No. 10/616,832, mailed May 12, 2010, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/667,144, mailed Nov. 23, 2009, Office Action.
U.S. Appl. No. 10/682,459, mailed Dec. 23, 2009, Office Action.
U.S. Appl. No. 10/682,459, mailed Apr. 28, 2010, Office Action.
U.S. Appl. No. 10/786,444, mailed Jan. 14, 2010, Office Action.
U.S. Appl. No. 10/787,073, mailed Feb. 17, 2010, Notice of Allowance.
U.S. Appl. No. 10/908,721, mailed Feb. 2, 2010, Office Action.
U.S. Appl. No. 11/048,503, mailed Jan. 11, 2010, Notice of Allowance.
U.S. Appl. No. 11/048,503, mailed Apr. 26, 2010, Notice of Allowance.
U.S. Appl. No. 11/316,775, mailed Apr. 16, 2008, Restriction Requirement.
U.S. Appl. No. 11/316,775, mailed Aug. 6, 2008, Office Action.
U.S. Appl. No. 11/344,891, mailed May 7, 2010, Office Action.
U.S. Appl. No. 11/396,141, mailed May 4, 2010, Office Action.
U.S. Appl. No. 11/406,203, mailed Jun. 18, 2010, Notice of Allowance.
U.S. Appl. No. 11/455,993, mailed Feb. 17, 2009, Office Action.
U.S. Appl. No. 11/455,993, mailed Dec. 16, 2009, Office Action.
U.S. Appl. No. 11/508,656, mailed Dec. 9, 2009, Restriction Requirement.
U.S. Appl. No. 11/508,656, mailed Mar. 25, 2010, Office Action.
U.S. Appl. No. 11/508,662, mailed Dec. 28, 2009, Restriction Requirement.
U.S. Appl. No. 11/508,662, mailed Apr. 14, 2010, Office Action.
U.S. Appl. No. 11/508,715, mailed Jan. 6, 2010, Restriction Requirement.
U.S. Appl. No. 11/508,715, mailed Apr. 26, 2010, Office Action.
U.S. Appl. No. 11/532,325, mailed Jan. 5, 2010, Office Action.
U.S. Appl. No. 11/532,576, mailed Mar. 1, 2010, Restriction Requirement.
U.S. Appl. No. 11/532,576, mailed Apr. 23, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 11/675,462, mailed Dec. 10, 2009, Office Action.
U.S. Appl. No. 11/958,295, mailed May 25, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 11/959,334, mailed Apr. 14, 2010, Notice of Allowance.
U.S. Appl. No. 12/106,928, mailed May 10, 2010, Office Action.
U.S. Appl. No. 12/106,937, mailed Nov. 18, 2009, Office Action.
U.S. Appl. No. 12/113,851, mailed Apr. 27, 2010, Restriction Requirement.
U.S. Appl. No. 12/402,398, mailed Mar. 9, 2010, Restriction Requirement.
U.S. Appl. No. 12/402,398, mailed May 20, 2010, Office Action.
U.S. Appl. No. 12/403,256, mailed Dec. 16, 2009, Restriction Requirement.
U.S. Appl. No. 12/403,256, mailed Mar. 30, 2010, Office Action.
U.S. Appl. No. 29/296,370, mailed Feb. 10, 2010, Issue Notification.
U.S. Appl. No. 11/958,281, Mail Date Sep. 2, 2010, Office Action.
U.S. Appl. No. 10/264,306, Mail Date Oct. 29, 2010, Notice of Allowance.

U.S. Appl. No. 10/356,214, Mail Date Sep. 3, 2010, Notice of Allowance.
U.S. Appl. No. 10/435,104, Mail Date Oct. 5, 2010, Notice of Allowance.
U.S. Appl. No. 10/616,832, Mail Date Sep. 20, 2010, Notice of Allowance.
U.S. Appl. No. 10/682,459, Mail Date Oct. 12, 2010, Office Action.
U.S. Appl. No. 10/787,073, Mail Date Aug. 25, 2010, Notice of Allowance.
U.S. Appl. No. 10/787,073, Mail Date Sep. 15, 2010, Issue Notification.
U.S. Appl. No. 11/198,811, Mail Date Oct. 20, 2010, Issue Notification.
U.S. Appl. No. 11/406,203, Mail Date Oct. 6, 2010, Issue Notification.
U.S. Appl. No. 11/427,297, Mail Date Sep. 15, 2010, Office Action.
U.S. Appl. No. 11/532,576, Mail Date Oct. 13, 2010, Notice of Allowance.
U.S. Appl. No. 11/675,462, Mail Date Aug. 31, 2010, Office Action.
U.S. Appl. No. 11/852,190, Mail Date Nov. 1, 2010, Office Action.
U.S. Appl. No. 12/106,928, Mail Date Oct. 25, 2010, Office Action.
U.S. Appl. No. 12/114,031, Mail Date Oct. 5, 2010, Office Action.
U.S. Appl. No. 12/403,277, Mail Date Oct. 12, 2010, Office Action.
U.S. Appl. No. 12/114,091, Mail Date Oct. 27, 2010, Office Action.

* cited by examiner

SURGICAL STAPLE

CROSS-REFERENCE TO RELATED APPLICATIONS

This application is a continuation of U.S. patent application Ser. No. 10/240,183 filed on Sep. 27, 2002 and entitled "Surgical Staple," which claims priority to International Application PCT/IE02/00078 filed on Jun. 4, 2002 and entitled "Surgical Staple," which claims priority to Irish Application No. S2001/0547 filed on Jun. 7, 2001 and entitled "Surgical Staple," which are hereby incorporated by reference in their entirety.

FIELD OF THE INVENTION

This invention relates to a surgical staple.

BACKGROUND OF THE INVENTION

Staples have been used in general surgery for many years, mainly for anastomosing tissue. Examples include skin staplers used to close a skin incision in place of the standard manual suturing process, and end-to-end and end-to-side bowel stapling instruments which are generally one shot devices used during bowel reconstruction procedures.

The staples used with these devices are generally manufactured from a metal or metal alloy material such as stainless steel or titanium. The majority are constructed from round profile wire and generally produced in a generally 'U'-shaped configuration. The ends of the 'U'-shape are normally pointed or sharpened so as to ensure easy tissue penetration. Examples of prior art in this area include U.S. Pat. Nos. 4,505,273, 5,026,390 and 4,719,917.

In clinical use the staples are delivered using a stapler device which generally consists of an anvil component positioned inside the 'U' between staple legs and in contact with the staple. A former component is positioned on the other side of the staple base, the gap between the forming arms of the former being approximately the width of the anvil plus two times the diameter of the staple wire. The head of the stapler device is normally positioned centrally across the slit or opening which is to be closed.

On activation of the device the staple legs are advanced forward so that they penetrate the tissue on both sides of the slit or opening. As the former is advanced further the legs of the staple bend around the anvil causing the tips of the legs to advance along an arcuate path toward each other so that the staple ultimately assumes a generally rectangular shape thereby compressing the tissue which has been trapped between the staple legs. This compression of tissue is the mechanism by which a closure is effected. Depending on the length of the incision or opening a series of staples will be delivered along its length in order to ensure a blood tight closure.

While this method of closing an incision is effective when a series of staples are used along the length of the incision it is less effective when it is desirable to close the opening with the minimum number of staples. For example for an incision of 5-6 mm in length one round wire staple positioned centrally along the incision is insufficient to effect a closure as the compression due to the staple legs only acts in a limited area towards the center of the incision, leaving the extremities open.

Also in situations where the tissue is soft and friable the narrow staple leg will have a tendency to tear through the tissue as they are bent around the anvil thereby decreasing the level of compression between the staple legs and causing unnecessary damage to the vessel wall.

In order to avoid complications such as clot formation, it is important to retain the staple legs within the vessel wall, i.e. avoid the penetration of the internal wall on the introduction of a foreign body into the lumen of the vessel. If the staple legs penetrate into the lumen of the vessel there is the added danger that excessive pressure from the staple gun may cause the vessel to collapse, which can lead to the legs penetrating the opposing vessel wall, i.e. stapling the vessel walls together and blocking the lumen of the vessel.

Therefore there is a need for an improved surgical staple which will more effectively close an incision, thereby requiring fewer staples to close an incision. In addition it would be advantageous to profile the staple legs so that they are less inclined to tear through softer tissue. Furthermore, it would be desirable to limit the depth of penetration of the staple legs to prevent the legs entering the lumen of the vessel.

SUMMARY OF THE INVENTION

Accordingly, the present invention provides a surgical staple comprising a base and a pair of legs each extending from an opposite end of the base, each leg having a penetrative portion terminating at a tip, the staple being deformable to bend each leg relative to the base causing each tip to approach the other leg along a substantially arcuate path lying in a plane, wherein each leg further comprises a compressive portion located intermediate the base and the penetrative portion, the compressive portion having a height greater than that of the penetrative portion, said heights being measured in the direction perpendicular to the plane defined by the arcuate path.

The advantage of the invention is that the improved surgical staple delivers a significantly increased area of compression between the staple legs once the staple has been deformed in use. The increased area of compression is achieved by providing the compression portion which tends to increase the contact area between the staple and the tissue against which it is bearing.

The invention is particularly useful in applications where the staple is permanently implanted inside the body. In such cases it is desirable to minimize the amount of metal which is needed to effect a positive closure. With existing stapler devices a series of staples need to be positioned along the length of the slit or tissue edges being anastomosed. Staples are normally positioned close together as any one staple will only compress a small amount of tissue on either side. Using staples with an improved compression capacity, as provided by this invention, will mean that a significantly lower number of staples is required to close any one incision.

The invention also has particular relevance in the area of vascular puncture closure. During this percutaneous procedure it is desirable to close the arterial puncture preferably with one staple. Again it is desirable that the staple contains the minimum amount of metal. However, it is important that once delivered the staple has generated enough compression along the length of the slit or hole to prevent any blood leakage. The direction of height of the compression portion normal to the plane of closure of the legs corresponds in use to the direction of length along the incision.

BRIEF DESCRIPTION OF THE DRAWINGS

Embodiments of the invention will now be described, by way of example, with reference to the accompanying drawings, in which.

In the figures the same reference numerals have been used to indicate the same or equivalent components.

DETAILED DESCRIPTION OF THE INVENTION

Figure 1:
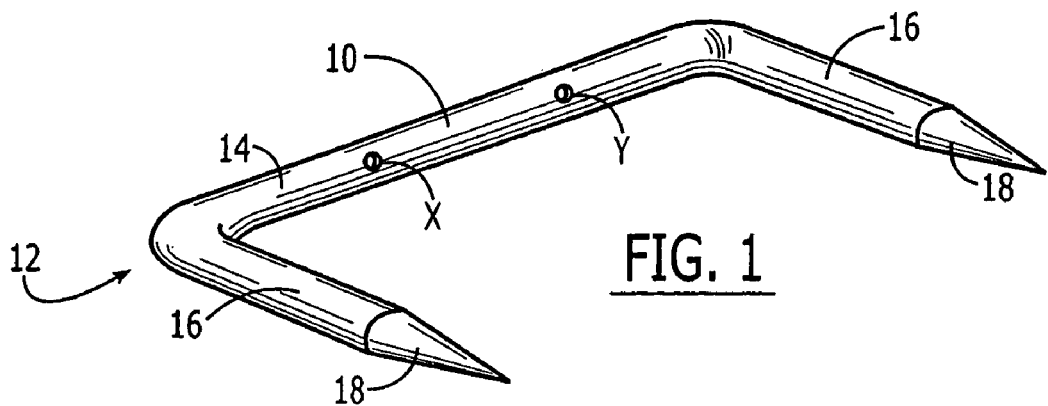
FIG. 1 is a perspective view of a conventional surgical staple.

Referring first to FIG. 1, a conventional round wire surgical staple is of a generally 'U'-shaped configuration, consisting of a base 10 and a pair of "L"-shaped legs 12 each having a proximal portion 14 forming a linear extension of the base before use (as shown in FIG. 1) and a distal portion 16 projecting substantially perpendicularly from the proximal portion.

The free ends 18 of the staple legs are generally sharpened so as to ensure easy tissue penetration. In addition to penetrating the tissue the staple is also formed in use, to bring the free ends of the legs together and thereby hold closed a wound. By forming the staple, the staple is transformed from a generally "U"-shaped configuration to a generally rectangular shaped configuration during the delivery process. This occurs by bending the legs 12 through 90° relative to the base 10 of the staple at the point where the proximal portions of the legs meet the base (known as the bend points and denoted as points X and Y in the drawings) at points relative to the central portion 10b.

Figure 2A:
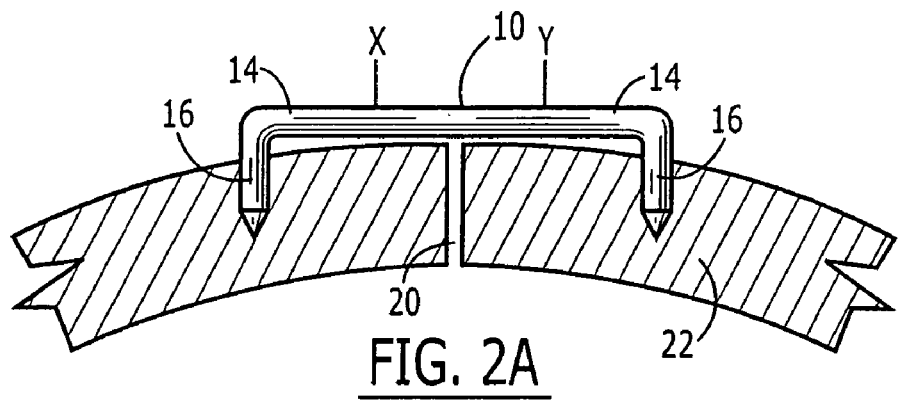
FIG. 2a is a sectional view of an unformed staple in a vessel wall.
Figure 2B:
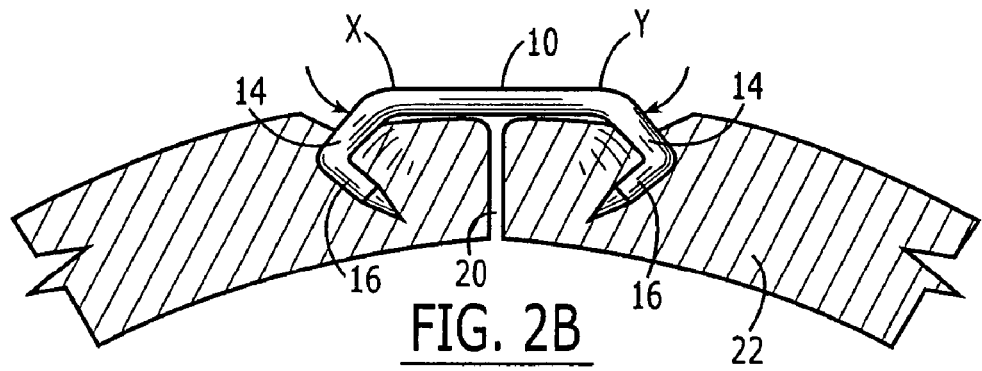
FIG. 2b is a sectional view of a partially formed staple in a vessel wall.
Figure 2C:
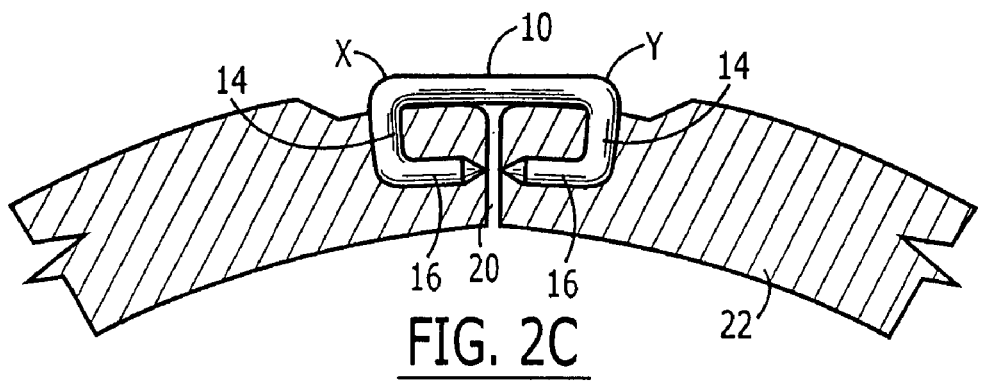
FIG. 2c is a sectional view of a staple fully formed in a vessel wall.

FIGS. 2(a) to 2(c) are a sequence of views showing the process by which the conventional staple is deployed and deformed from a generally "U"-shape to a generally rectangular shape to effect a closure of a puncture hole or slit 20 in a vessel or other tissue 22. In FIG. 2a the staple has been advanced from the delivery device (not shown) such that the distal portions of the staple legs 16 have punctured the tissue 22 and the staple base 10 and proximal portions 14 are lying against the outer surface of the tissue. In FIG. 2b the forming process has begun and the staple is being deformed around bend points X and Y causing the proximal portions 14 and distal portions 16 to arc through an angle of approximately 90° thereby compressing the tissue which is being captured between both staple legs. In FIG. 2c the staple has been fully formed into a rectangular shape, the tissue contained within the rectangle being compressed as a result of the staple legs having arced through approximately 90°.

Figure 3A:
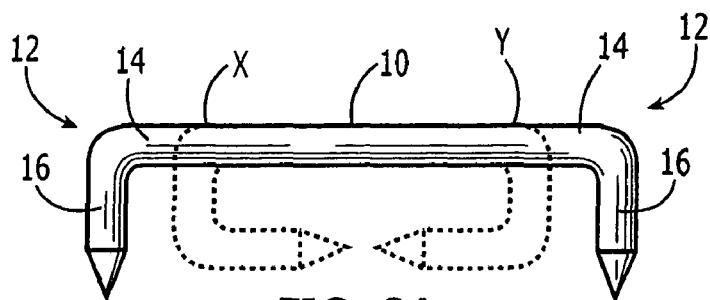
FIG. 3a is a plan view of a staple before and after forming.
Figure 3B:
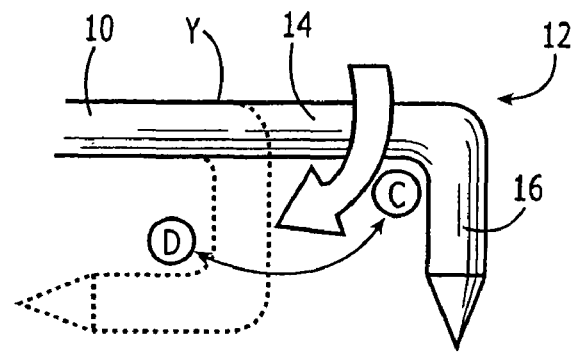
FIG. 3b is an enlarged view of a staple leg before and after forming.

In FIGS. 3a and 3b, the staple is shown prior to forming (dashed lines) and after forming (solid lines). As seen particularly in FIG. 3b, it can be seen that prior to forming and following penetration of the staple leg 12 into the tissue wall that there is an area of tissue captive in the region (c). After the forming process, i.e. when proximal portion 14 and distal portion 16 have arced through 90° at the bend point Y, the tissue which was previously captive at point (c) has now moved to point (d). The same process of compression occurs on the opposite leg of the staple thereby creating compressed tissue 24 (FIG. 4) within the rectangular shape of the formed staple.

Figure 4:
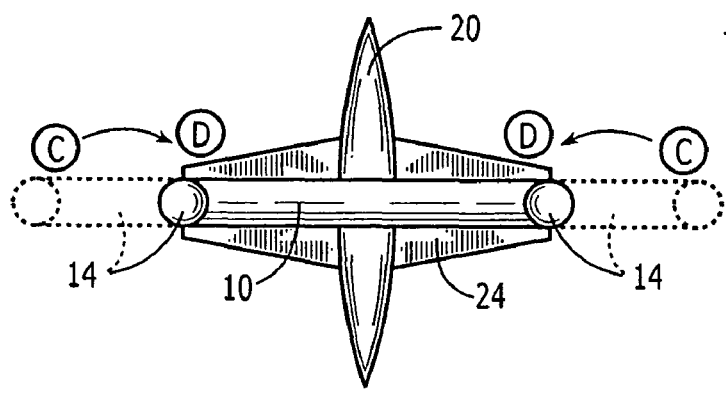
FIG. 4 is a plan view of a staple in position across a tissue opening.

In FIG. 4, the same compression process can be seen in plan view, the tissue which was captive inside the legs 12 at points (c) prior to forming has been moved to point (d) as a result of the staple forming process. However, the level of compression which has transferred to the hole 20 in the tissue is related to the area of surface contact between the staple leg and the tissue at points (c) and (d). With conventional round wire staples this contact area is quite small and therefore delivers a limited amount of compression over the length of the hole opening or slit in the tissue. Also, with round wire and leg to cut its way through softer tissue as opposed to compressing the tissue ahead of it.

The invention solves this problem by increasing the height of a portion of the legs 12 (i.e. the height being the dimension perpendicular to the plane in which the staple legs bend during forming), in order to increase the effective contact area between the staple legs and the tissue as the staple is being deformed. Increasing the contact area in this way will help prevent the staple leg from tearing its way through the tissue but more importantly will create a much greater area of compression within the rectangle of the formed staple and radiating from it, so that this compression will be transferred over a much greater length of the slit or opening 20 in the tissue.

Figure 5:
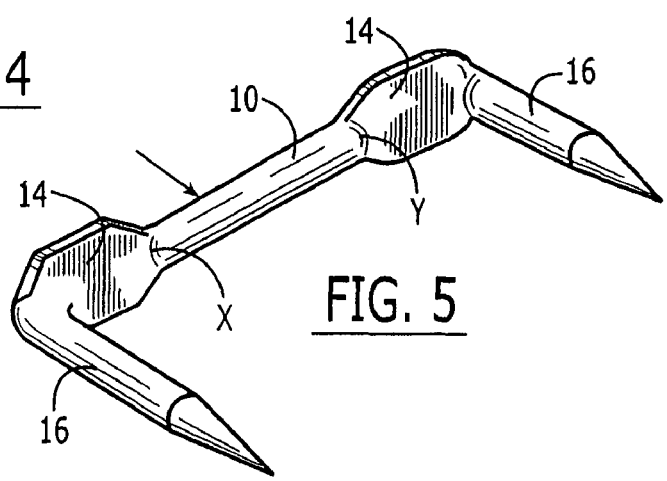
FIGS. 5 to 9 are perspective views of embodiments of the invention.

FIG. 5 is a perspective view of a first embodiment of surgical staple according to the invention. Here the proximal portion 14 of the legs of the conventional round wire staple described above have been deformed from a round to a flat, rectangular cross-section, providing a compressive portion located between the penetrative portion of the legs (which in this case is the entire distal portion 16). As mentioned, the purpose of this compressive portion is to increase the surface contact area between the staple legs and tissue in the direction in which the tissue is being compressed as the staple leg arcs through approximately 90° at its bend point.

Figure 6:
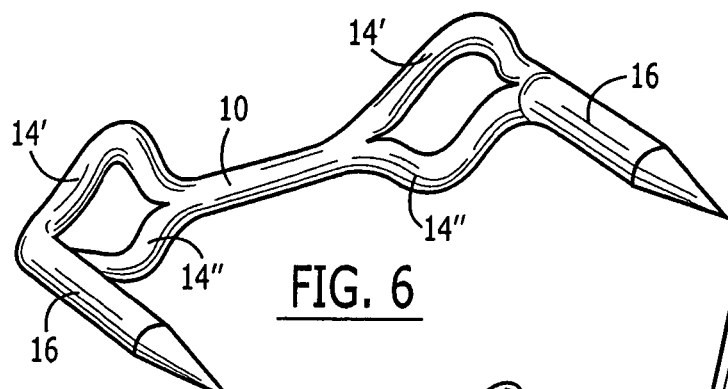

FIG. 6 shows another embodiment, in which the staple legs have been divided along the axis of the proximal portions and the opposite divisions 14' and 14" deformed apart so as to significantly increase the overall height of the proximal portions of the legs.

Figure 7:
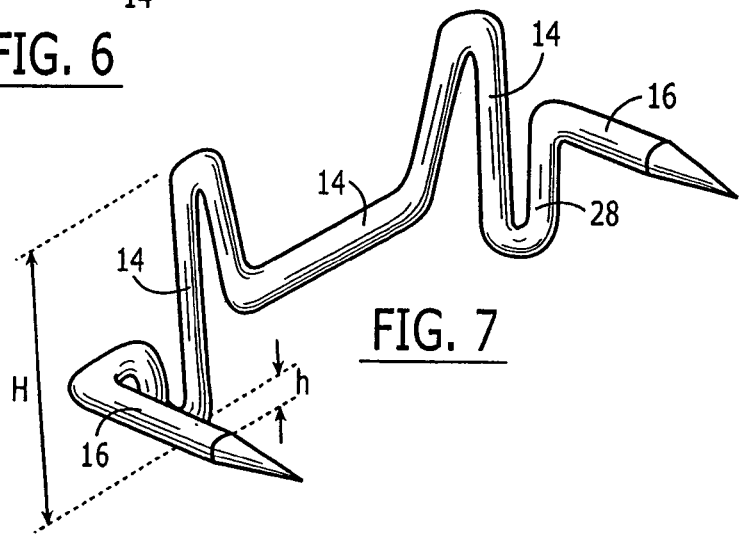

In FIG. 7 another round wire embodiment of the staple is shown. In this staple the wire in the proximal portion 14 of each leg is bent sinusoidally out of alignment with the base 10 to provide a compressive portion whose height H is significantly greater than the height h of the penetrative portion of the leg 16, again for the purpose of increasing the area of compression, and preventing the proximal portion from entering the wound. In the latter regard, it can be seen that the leading section 28 of the sinusoidally bent proximal portion extends generally at right angles from the penetrative portion 16. This provides a slightly rounded step or shoulder to act as a depth stop, defining the end of the penetrative portion of the leg and the start of the compressive portion.

Figure 8:
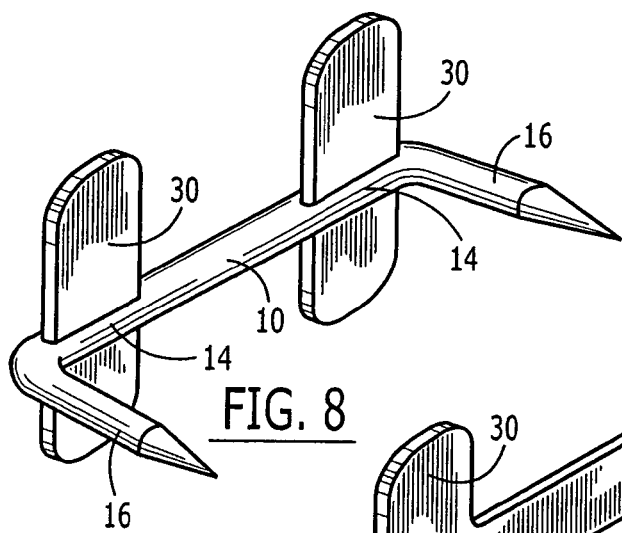
Figure 9:
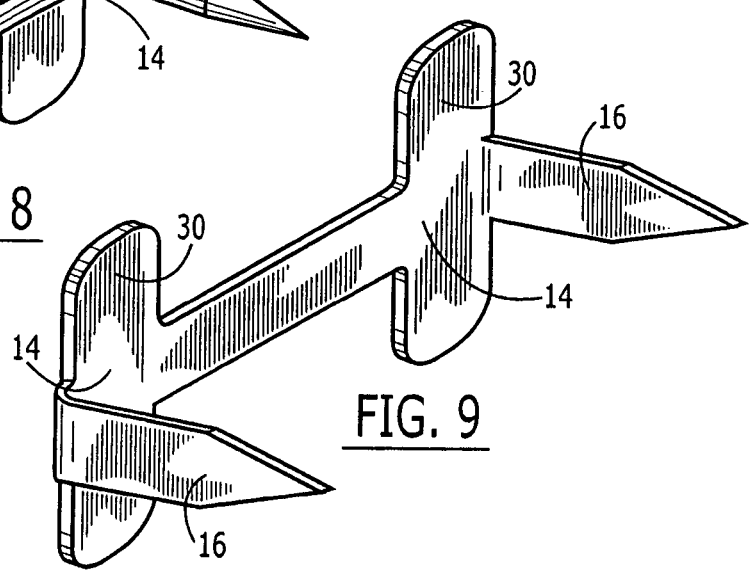

FIG. 8 shows an embodiment which consists of a standard round wire staple with flat plates or wings 30 attached to the proximal portion of the legs. FIG. 9 shows another staple similar to that of FIG. 8 which is manufactured from flat metal stock and bent. Again the staple legs include wings 30 such that the height of these wings is significantly greater than the height of the penetrative portion 16 of the staple legs.

Figure 10:
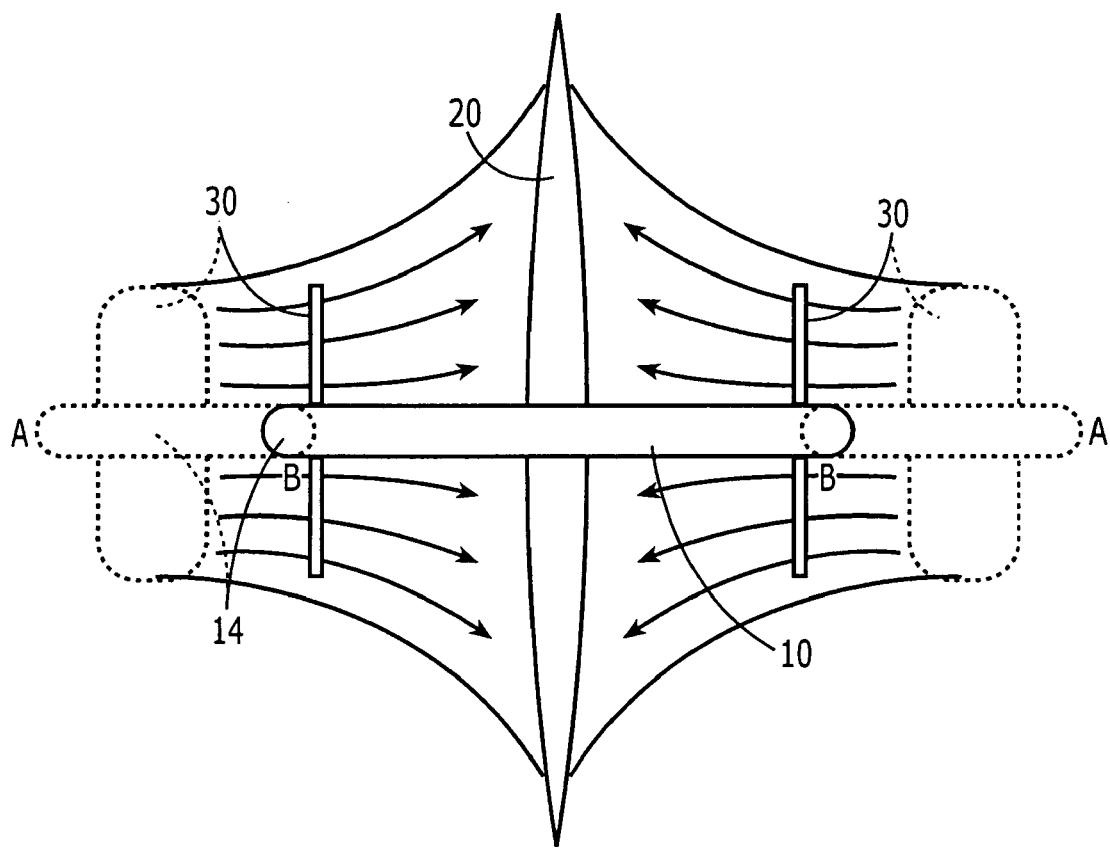
FIG. 10 is a plan view of the staple of FIG. 9 in position across a tissue opening.

The process by which these improved staples achieve greater areas of compression over the length of an opening in body tissue is illustrated in FIG. 10. FIG. 10 shows a staple of the kind illustrated in FIG. 8 but the same principle applies to all the staples of FIGS. 5 to 9. It can be seen that as the staple legs move from their open position at 'A' to their closed position at 'B' tissue 24 is compressed ahead of the wings 30 and this compression radiates over a much greater length of the slit or opening 20 than would be the case if the wings were not attached to the staple legs.

Figure 11:
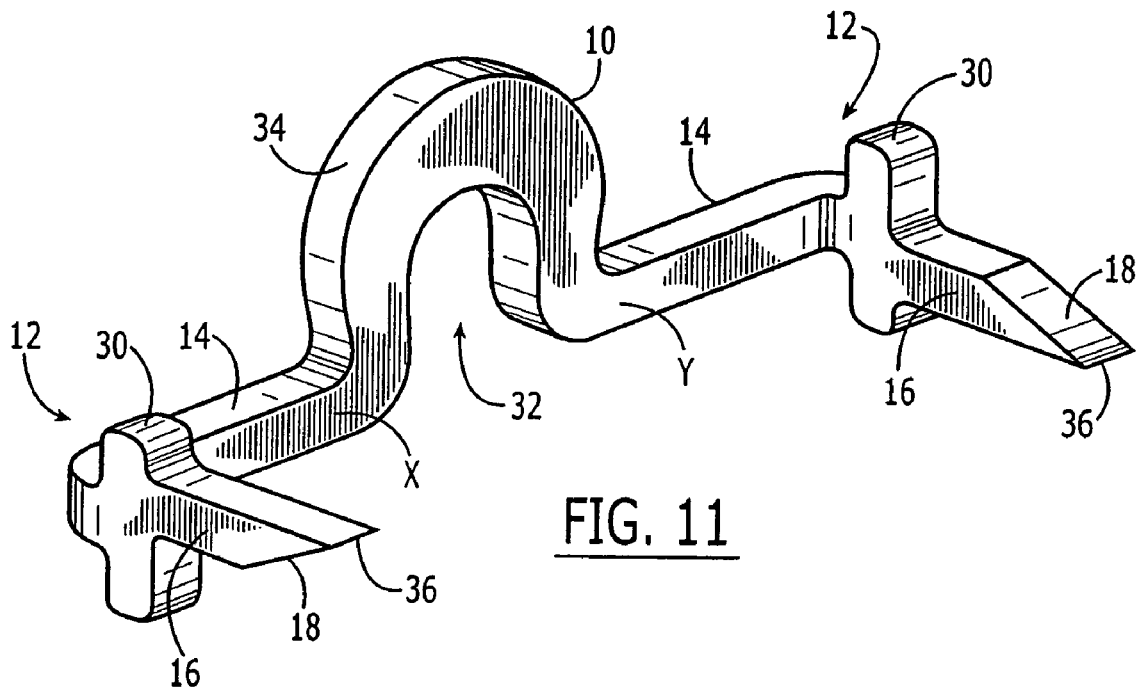
FIGS. 11 and 12, FIGS. 13 and 14, and FIGS. 15 and 16, respectively, are further perspective views of three additional embodiments of staple, each shown before and after forming.

FIG. 11 shows a staple stamped from a flat sheet and bent into its initial configuration (rather than a wire staple as previously described). The base 10 of the staple is horseshoe shaped rather than a flat linear base. The horseshoe shape defines a "U"-shaped opening 32 which allows the staple to sit on top of a blood locator tube extending from the end of a stapler. Such a stapler is described in WO 02/19922.

The stapler of WO 02/19922 takes the form of a hollow shaft and a blood locator tube slidable axially within the shaft. The tube projects beyond the end of the shaft to enter a puncture site in a blood vessel, and blood flowing back through the tube and exiting the device indicates to the surgeon that the tip of the shaft (where the stapling head is located) is at the incision in the vessel. A surgical staple straddles the tube and is slidable thereon forwardly towards an anvil against which the staple may be deformed to staple together the opposite edges of the puncture site. A cam mechanism drives the staple forwardly along the tube into deforming engagement with the anvil and at the same time retracts the tube into the shaft in time to allow the legs of the staple to close onto the puncture site.

The staple of FIG. 11 is adapted for use with such a device in that "U"-shaped opening 32 is adapted to straddle and slide on the blood locator tube.

The staple has a pair of legs 12 extending from the ends of the base 10. Each leg is generally "L"-shaped in plan view and comprises a proximal portion 14 and a distal portion 16 terminating at a pointed tip 18. In use (see also FIG. 12), the base 10 is held by an anvil (not shown) while forming arms of the stapler (not shown) push the proximal portions forwardly deforming the staple at bend points X and Y. The blood locator tube is withdrawn during this formation to ensure that as the tips 18 approach one another (ultimately coming to rest in the configuration of FIG. 12), they do not catch the locator tube.

Located on the distal portion 16 is a compressive portion 30 in the form of a bar extending at right angles to the distal portion. In this staple, therefore, the compressive portion and the penetrative portion are both located on the distal portion of the "L"-shaped leg. The penetrative portion is the part of the leg extending from the bar 30 to the tip 18. The forward surface 30a of the bar provides a shoulder acting as a depth stop to prevent the leg penetrating the vessel wall too deeply. This feature can be used to ensure that the tip will not penetrate into the lumen of a blood vessel by designing the staple such that the distance between the front surface 30a and the extremity of the tip 18 is less than the vessel wall thickness. The bar also serves as a compressive feature spreading the compressive forces provided by the staple along a length of the incision corresponding to the height H of the bar 30 (FIG. 12) as opposed to just the lesser height h of the penetrative portion. The compression is also increased by the relatively small distance between the bars 30 when the staple is closed.

By making the staple from a sheet material rather than from wire, another significant advantage is obtainable. The thickness of the material of the base (measured between the internal surface of the opening 32 and the corresponding external surface 34) is not constant but instead increases to a maximum at the apex of the horseshoe. This strengthens the structure against a tendency for the curve to distort as the staple is being formed. It has been found that the action of the former and anvil bending the legs relative to the base tends to cause the horseshoe curve to open out or flatten somewhat. It will be appreciated that this can lead to the staple deploying incorrectly, as the legs tend to deviate from the "straight-ahead" orientation during closure. Adding extra material to the curve toward the top selectively reinforces the curve at this point of maximum strain during forming and counteracts the tendency to distort.

Figure 12:
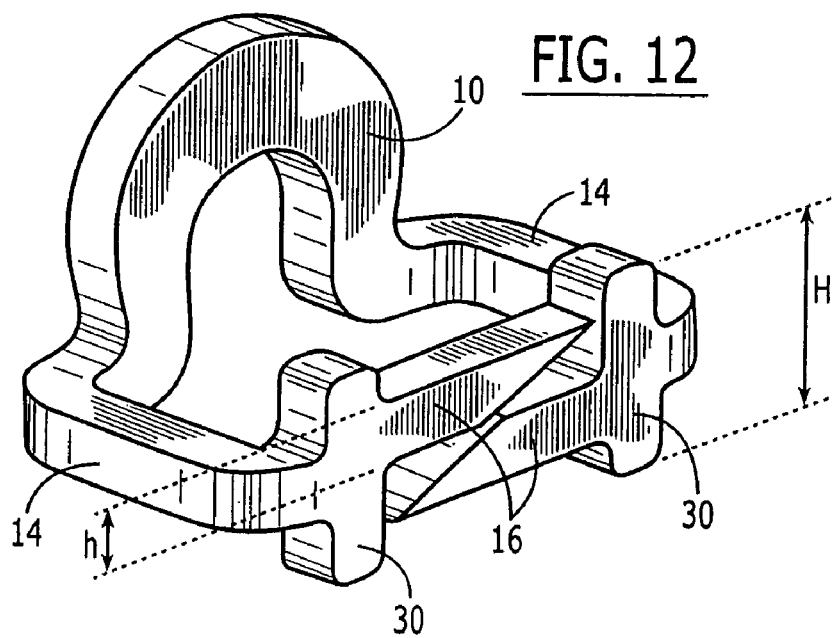

Another important feature of the staple of FIGS. 11 and 12 is that the staple is not symmetrical about the center line. The penetrative portions 16 are staggered vertically relative to one another so that one is disposed slightly above the line of the proximal portions and the other slightly below this line.

In addition, the respective tips 18 are beveled oppositely to one another so that the leading edge 36 of the tip on the left-hand penetrative portion (as viewed in FIG. 11) is significantly above the leading edge 36 of the right-hand tip. This double offset (staggering the respective penetrative portions and reversing the beveling of the tips) allows the two legs to close completely, so that the tips approach one another and pass one another when the staple is formed, providing greater compression and more reliable closure.

Figure 13:
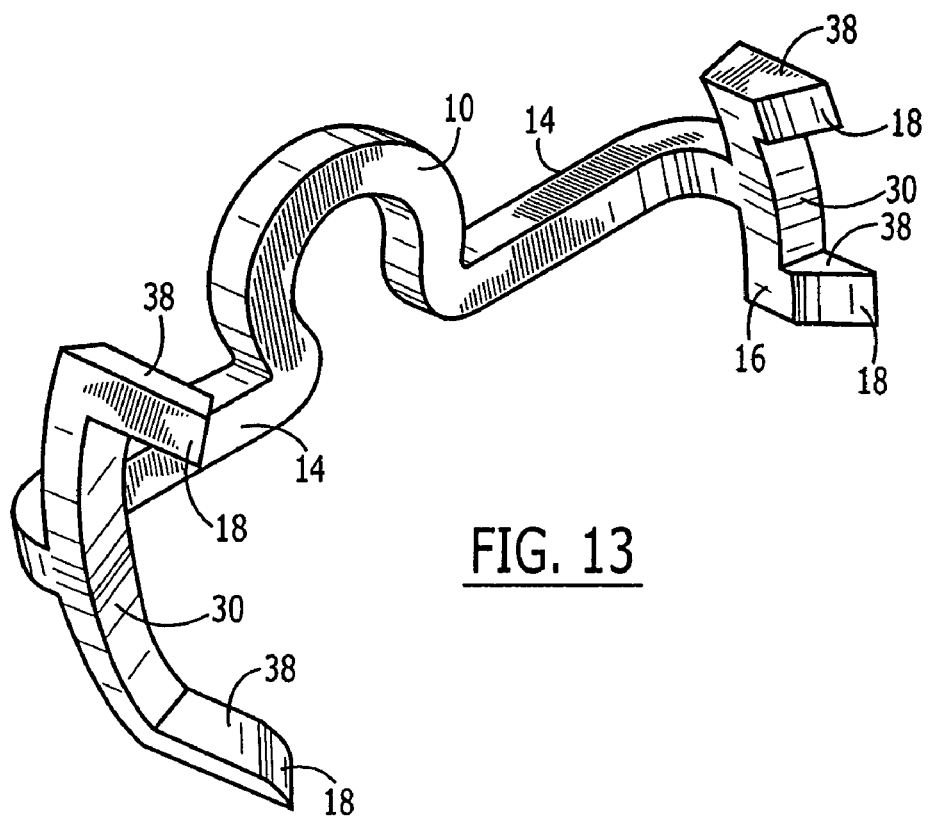
Figure 14:
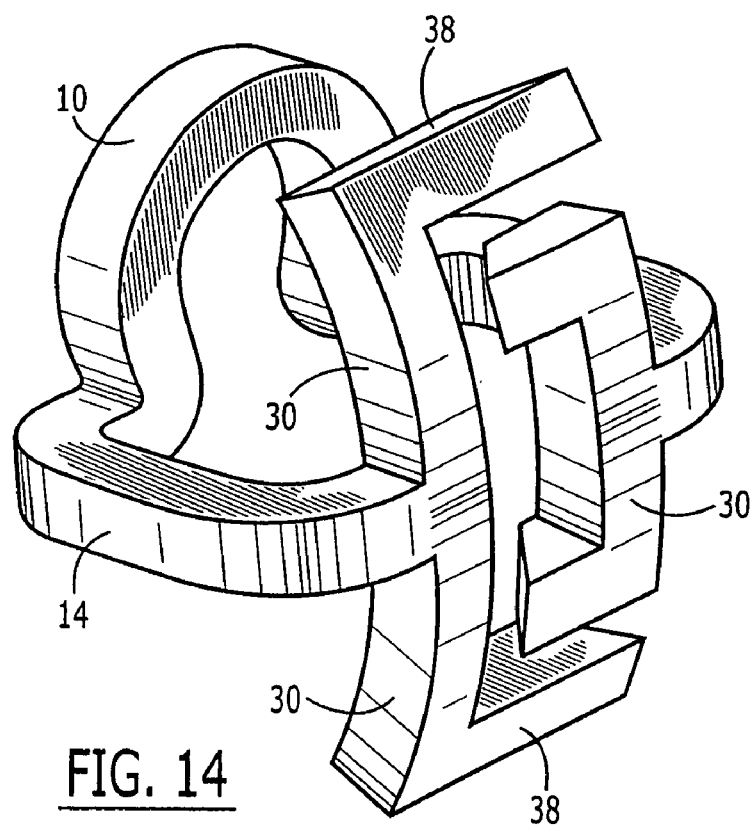

FIGS. 13 and 14 show a further embodiment of staple in open and closed configurations. The staple again has a base 10 with a leg 12 extending from each end. The base is horseshoe shaped, but in this case rather than there being additional material at the apex of the horseshoe curve, the curve assumes a slight omega (Ω) shape with the ends of the curve pointing inwards to counteract straightening tendencies.

Each leg 12 branches to a pair of tips 18 each having a penetrative portion 38. The two penetrative portions on each leg extend from the ends of a respective compressive portion 30 in the form of a curved bar which is generally perpendicular to both the proximal portion 14 and the penetrative portions 38. The bar 30 provides a shoulder acting as a depth stop and acts to spread the compressive forces of the staple along its length.

It can be seen from FIG. 14 that the legs are once again asymmetrical with respect to one another. The penetrative portions 38 of the left-hand leg are both longer and further separated from one another than those of the right-hand leg. Again this ensures that the two legs do not interfere with one another during closure and that the staple can form a fully closed structure when viewed in plan (see by comparison FIG. 2C in which there is a gap between the respective tips of the prior art staple, and the curve appears open in plan as a consequence.

The reason for the curvature of the bars 30 in the embodiment of FIGS. 13 and 14 is that the stapler for which it is designed has a round profile. In general it is desired to make the cross-sectional area of the stapler shaft as small as possible to minimize trauma arising from the introduction of the stapler. The shape of this embodiment of staple therefore allows the staple to fit in a rounded shaft while allowing the compressive portions (bars 30) to grip the sides of the wound as widely as possible, as will be appreciated with reference to FIG. 10.

Figure 15:
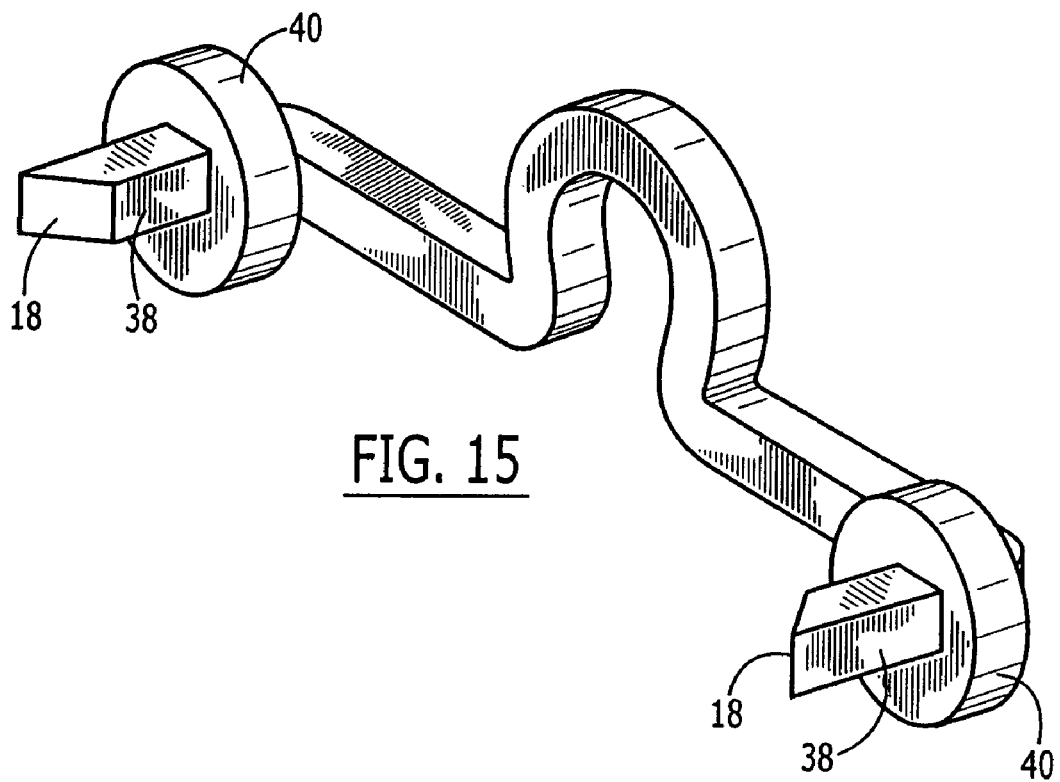
Figure 16:
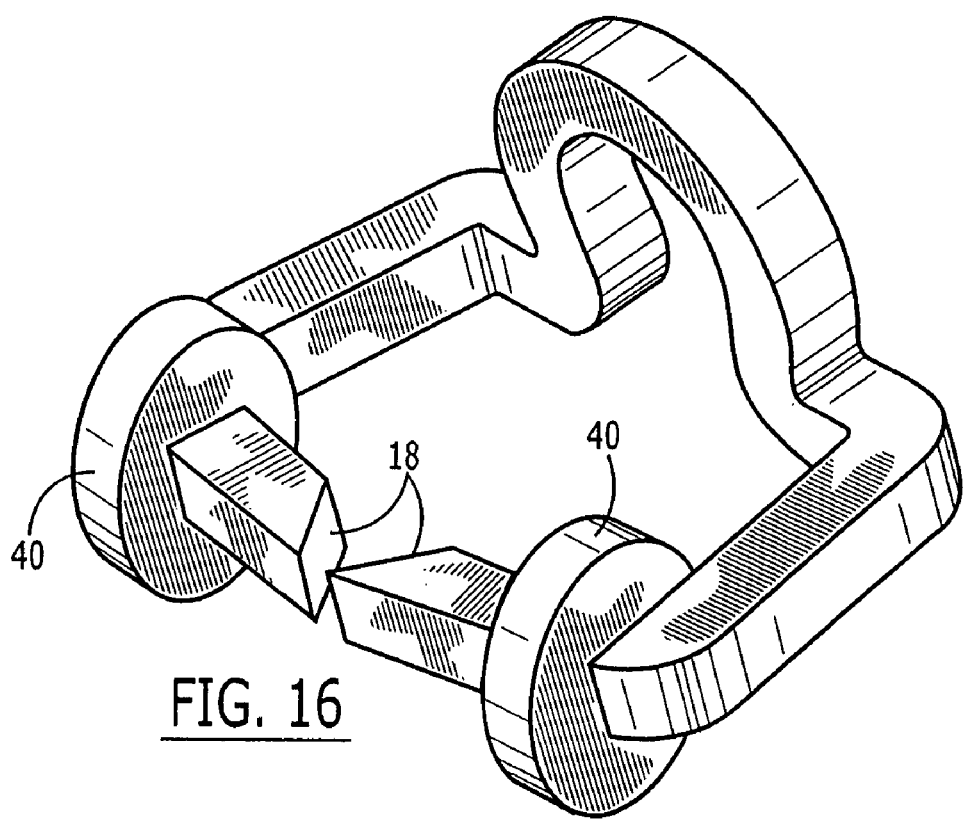

FIGS. 15 and 16 provide yet another embodiment in which the penetrative portions 38 of the legs 12 extend between the tip 18 and a shoulder of a compressive portion of the leg which in this case is provided by a disk 40 mounted on the distal portion of each leg.

The embodiments described herein have "L"-shaped legs with a roughly 90° angle between proximal and distal sections. It will be noted that the compressive section can be on either the proximal section or the distal section. Furthermore, the legs need not take this "L"-shape and can instead be curved (e.g. in a quarter-circle), with the portion of leg adjacent the tip defining a penetrative portion and a compressive structure being located further along the curve towards the base.

To aid in staple formation the point at which the legs join the base can be weakened or provided by a notch, but in most cases this is unnecessary as the deformation between the anvil and former will cause the legs to bend correctly at the junction with the base.

The invention is not limited to the embodiments described herein which may be modified or varied without departing from the scope of the invention.

What we claim is:

1. A method for closing an incision, comprising:

advancing opposed legs of an undeformed surgical staple toward an incision to position a base of the staple extending between the opposed legs across the incision and to cause penetrative tips of the legs to penetrate through tissue on opposed sides of the incision; and deforming the surgical staple to move at least a portion of each leg within a plane to cause the penetrative tips of the opposed legs to advance toward one another along a substantially arcuate path and to pass one another to close completely, each of the legs having a leg dimension in a first direction perpendicular to and extending from the plane, at least a portion of the base being in the plane and the base having a base dimension in the first direction, each leg further including a compressive portion formed thereon that acts as a depth stop to limit a penetration depth of each leg through the tissue, the compressive portion having a compressive dimension in the first direction, the compressive dimension being greater than the leg dimension, wherein at least one of the penetrative tips substantially abuts at least one of the compressive portions when the penetrative tips are closed completely.

2. The method of claim 1, wherein the compressive portion on each leg is formed between a proximal portion and the penetrative tip of each leg.

3. The method of claim 1, wherein the compressive portion on each leg has a cross-sectional area greater than that of the penetrative tip.

4. The method of claim 1, wherein each leg includes two penetrative tips formed thereon and connected to one another by the compressive portion.

5. The method of claim 4, wherein each compressive portion is in the form of a bar extending substantially perpendicular to the proximal portion of the leg.

6. The method of claim 1, wherein the penetrative tip on one leg is staggered from the penetrative tip of the other leg to allow the penetrative tips to pass one another.

7. The method of claim 1, wherein at least a portion of the base includes an arc formed therein.

8. The method of claim 7, wherein the arc extends substantially transverse to a plane containing a proximal portion of each leg.

9. The method of claim 7, wherein the opposed legs of the surgical staple are advanced toward an incision by positioning the arc of the base around a shaft, and advancing the surgical staple along the shaft.

10. The method of claim 1, wherein deforming the surgical staple comprises bending each leg relative to the base.

11. A method for closing an incision, comprising:

positioning a base of an undeformed surgical staple across an incision formed in tissue;

advancing at least two legs extending from opposed ends of the base toward the tissue to cause a penetrative portion of each leg to extend through the tissue on opposed sides of the incision; and deforming the surgical staple to move at least a portion of each leg within a plane by bending each leg relative to the base to cause the penetrative portions of each leg to advance toward one another and to cause a compressive portion formed on each leg to engage and compress the tissue and thereby limit penetration of the penetrative portion of each leg into the tissue, each of the legs having a leg dimension in a first direction perpendicular to and extending from the plane, at least a portion of the base being in the plane and having a base dimension in the first direction, the compressive portion having a compressive dimension in the first direction, the compressive dimension being greater than the leg dimension wherein at least one of the penetrative tips substantially abuts at least one of the compressive portions when the penetrative tips are closed completely.

12. The method of claim 11, wherein each leg is bent relative to the base about a corresponding bend point and the compressive portion on each leg is formed between the bend point and the penetrative portion of each leg.

13. The method of claim 11, wherein the compressive portion on each leg has a cross-sectional area greater than that of the penetrative portion.

14. The method of claim 11, wherein the penetrative portion of each leg comprises two penetrative tips that are connected to one another by the compressive portion.

15. The method of claim 14, wherein each compressive portion is in the form of a bar extending substantially perpendicular to the proximal portion of the leg.

16. The method of claim 11, wherein the penetrative portion on one leg is staggered from the penetrative portion of the other leg to allow the penetrative portions to pass one another.

17. The method of claim 11, wherein at least a portion of the base includes an arc formed therein.

18. The method of claim 17, wherein the arc extends substantially transverse to a plane containing a proximal portion of each leg.

19. The method of claim 17, wherein the opposed legs of the surgical staple are advanced toward an incision by positioning the arc of the base around a shaft, and advancing the surgical staple along the shaft.

20. The method of claim 11, wherein deforming the surgical staple causes the penetrative portions of each leg to pass one another.

21. A method for closing an incision, comprising:

advancing opposed legs of an undeformed surgical staple toward an incision to position a base of the staple extending between the opposed legs across the incision and to cause penetrative tips of the legs to penetrate through tissue on opposed sides of the incision, the opposed legs extending at an angle from each end of the base and terminating at a free end, the base and the legs lying in substantially a common plane; and deforming the surgical staple to move at least a portion of each leg within the common plane by bending each leg relative to the base to cause the penetrative tips of the opposed legs to advance toward one another along a substantially arcuate path, each of the legs having a leg dimension in a first direction perpendicular to and extending from the common plane, the base having a base dimension in the first direction, each leg further includes a compressive portion formed thereon that acts as a depth stop to limit a penetration depth of each leg through the tissue, the compressive portion having a compressive dimension in the first direction, the compressive dimension being greater than the leg dimension, wherein at least one of the penetrative tips substantially abuts at least one of the compressive portions when the penetrative tips are closed completely.

22. The method of claim 21, wherein deforming the surgical staple causes the penetrative tips of the opposed legs to pass one another to close completely.

23. The method of claim 21, wherein each leg is bent relative to the base about a corresponding bend point and the compressive portion on each leg is formed between the bend point and the penetrative tip of each leg.

* * * * *